US012572074B2

(12) United States Patent
Endo et al.

(10) Patent No.: US 12,572,074 B2
(45) Date of Patent: Mar. 10, 2026

(54) RESIST UNDERLYING FILM-FORMING COMPOSITION COMPRISING A REACTION PRODUCT WITH A GLYCIDYL ESTER COMPOUND

(71) Applicant: NISSAN CHEMICAL CORPORATION, Tokyo (JP)

(72) Inventors: Takafumi Endo, Toyama (JP); Yuichi Goto, Toyama (JP); Masahisa Endo, Toyama (JP); Satoshi Kamibayashi, Toyama (JP); Yuki Endo, Toyama (JP)

(73) Assignee: Nissan Chemical Corporation, Tokyo (JP)

( * ) Notice: Subject to any disclaimer, the term of this patent is extended or adjusted under 35 U.S.C. 154(b) by 810 days.

(21) Appl. No.: 17/254,562

(22) PCT Filed: Jun. 18, 2019

(86) PCT No.: PCT/JP2019/023991

§ 371 (c)(1),
(2) Date: Dec. 21, 2020

(87) PCT Pub. No.: WO2020/004122

PCT Pub. Date: Jan. 2, 2020

(65) Prior Publication Data

US 2021/0271168 A1 Sep. 2, 2021

(30) Foreign Application Priority Data

Jun. 26, 2018 (JP) ................................ 2018-121281

(51) Int. Cl.

| | |
|---|---|
| ***G03F 7/11*** | (2006.01) |
| ***C07D 405/14*** | (2006.01) |
| ***C08G 59/26*** | (2006.01) |
| ***C09D 163/00*** | (2006.01) |
| ***G03F 7/09*** | (2006.01) |
| ***G03F 7/16*** | (2006.01) |
| ***G03F 7/20*** | (2006.01) |
| ***G03F 7/30*** | (2006.01) |
| ***H01L 21/027*** | (2006.01) |
| ***H01L 21/308*** | (2006.01) |

(52) U.S. Cl.

CPC .............. *G03F 7/11* (2013.01); *C07D 405/14* (2013.01); *C08G 59/26* (2013.01); *C09D 163/00* (2013.01); *G03F 7/094* (2013.01); *H01L 21/0274* (2013.01); *H01L 21/3081* (2013.01); *G03F 7/162* (2013.01); *G03F 7/20* (2013.01); *G03F 7/30* (2013.01)

(58) Field of Classification Search

CPC . G03F 7/11; G03F 7/091; G03F 7/092; G03F 7/094; C08G 59/26; C08G 59/3236; C08G 59/4064; C08G 59/42; C08G 59/4207; C08G 59/423; C08G 59/4215; C08G 59/66

See application file for complete search history.

(56) References Cited

U.S. PATENT DOCUMENTS

| | | | | |
|---|---|---|---|---|
| 3,787,405 | A * | 1/1974 | Porret | C08G 59/26 523/450 |
| 2006/0290429 | A1 | 12/2006 | Kishioka et al. | |
| 2008/0206680 | A1 | 8/2008 | Kishioka et al. | |
| 2010/0009293 | A1 | 1/2010 | Yao et al. | |
| 2010/0009297 | A1 | 1/2010 | Yao et al. | |
| 2011/0033800 | A1 * | 2/2011 | Zampini | C07D 251/32 528/289 |

(Continued)

FOREIGN PATENT DOCUMENTS

| | | | | |
|---|---|---|---|---|
| JP | 08081461 | A | * | 3/1996 |
| JP | H08-081461 | A | | 3/1996 |

(Continued)

OTHER PUBLICATIONS

English translation of JP08081461. (Year: 1996).*
English translation of JP2009093162. (Year: 2009).*
Aug. 27, 2019 Search Report issued in International Patent Application No. PCT/JP2019/023991.

*Primary Examiner* — Mark F. Huff
*Assistant Examiner* — Anna Malloy
(74) *Attorney, Agent, or Firm* — Oliff PLC

(57) ABSTRACT

A resist underlayer film having a particularly high dry etching rate; a resist underlayer film-forming composition; a resist pattern forming method; and a semiconductor device production method. The resist underlayer film-forming composition contains a solvent and an epoxy adduct obtained by reacting a compound represented by formula (1) and an epoxy adduct-forming compound. The epoxy adduct-forming compound is one or more compounds selected from the group made of carboxylic acid-containing compounds, carboxylic anhydride-containing compounds, hydroxy group-containing compounds, thiol group-containing compounds, amino group-containing compounds, and imide group-containing compounds.

Formula (1)

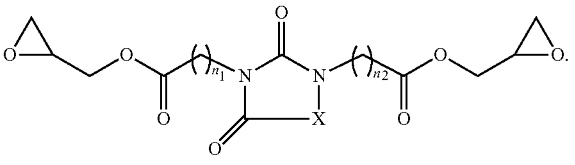

13 Claims, No Drawings

(56) References Cited

U.S. PATENT DOCUMENTS

| | | | | |
|---|---|---|---|---|
| 2011/0053091 | A1* | 3/2011 | Hiroi | C08G 59/186<br>252/582 |
| 2020/0117088 | A1* | 4/2020 | Shin | G03F 7/0233 |

FOREIGN PATENT DOCUMENTS

| | | | | |
|---|---|---|---|---|
| JP | 2009093162 | A | * | 4/2009 |
| JP | 2011-527460 | A | | 10/2011 |
| JP | 2011-527461 | A | | 10/2011 |
| WO | 2004/034148 | A1 | | 4/2004 |
| WO | 2009/096340 | A1 | | 8/2009 |
| WO | 2013/161862 | A1 | | 10/2013 |
| WO | 2014/002861 | A1 | | 1/2014 |

* cited by examiner

RESIST UNDERLYING FILM-FORMING COMPOSITION COMPRISING A REACTION PRODUCT WITH A GLYCIDYL ESTER COMPOUND

TECHNICAL FIELD

The present invention relates to a composition for forming a resist underlying film having especially high dry etching rate, a resist underlying film using the resist underlying film-forming composition and a method for producing the same, a method for forming a resist pattern, and a method for producing a semiconductor device.

BACKGROUND ART

When a resist film is subjected to exposure, reflected waves can adversely affect the resist film. A resist underlying film formed for the purpose of suppressing the adverse effect is called also an antireflection film.

A demand is made on the resist underlying film such that the film can be easily formed merely by applying a resist underlying film-forming composition in the form of a solution and curing the composition. Therefore, the composition for forming the resist underlying film needs to contain a compound (polymer) which is readily curable by, for example, heating and which has a high solubility in a predetermined solvent.

It is desirable that the resist pattern formed on the resist underlying film has a cross-section, taken along the direction perpendicular to the substrate, which is rectangular (straight bottom form free from the so-called undercut, footing and others). For example, a resist pattern having an undercut or footing profile would cause problems of collapsing of the resist pattern and preventing the processing of a material to be processed (such as a substrate or an insulating film) into a desired form or size in the lithography step.

Further, a resist underlying film is required to have a larger dry etching rate, i.e., a larger selective ratio for dry etching rate, than that of a resist film formed thereon.

Patent Literature 1 discloses a resist underlying film-forming composition using a polymer having a disulfide linkage in the principal chain thereof. Patent Literature 2 discloses an epoxy compound having a glycidyl ester group. Patent Literature 3 discloses an antireflection film-forming composition comprising a triazinetrione compound, oligomer compound, or polymer compound having a hydroxyalkyl structure as a substituent on a nitrogen atom.

CITATION LIST

Patent Literatures

Patent Literature 1: JP 2009-096340 A
Patent Literature 2: JP H08-81461 A
Patent Literature 3: WO 2004/034148 A1

SUMMARY OF INVENTION

Technical Problem

In the production of semiconductor elements, a resist underlying film having a high dry etching rate has been still desired. It has been known that a resist underlying film having a high dry etching rate is obtained by applying a polymer containing a heteroatom to the polymer used in the composition for forming the film.

The present inventors have conducted extensive and intensive studies, and have made studies on various types of compounds and reaction products thereof (oligomers and polymers) with a view to obtaining a resist underlying film containing a heteroatom in a higher concentration. As a result, it has been found that a higher etching rate than that obtained by a conventional technique can be achieved by applying a specific epoxy addition product obtained by reacting a nitrogen-containing heterocyclic compound having a glycidyl ester group (such as isocyanuric acid) and an epoxy addition product-forming compound, such as a carboxylic acid, to a resist underlying film-forming composition.

In view of solving the above-mentioned problems, an object of the present invention is to provide a composition for forming a resist underlying film having an especially high dry etching rate. Another object of the present invention is to provide a resist underlying film using the resist underlying film-forming composition and a method for producing the same, a method for forming a resist pattern, and a method for producing a semiconductor device.

Solution to Problem

The present invention embraces the followings.

[1] A compound represented by the following formula (1):

[Chemical formula 1]

Formula (1)

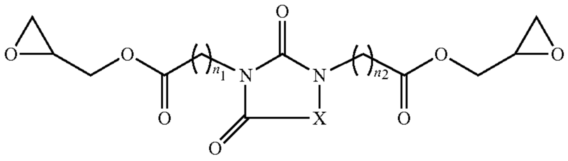

wherein, in formulae (1), X is a divalent organic group represented by formula (2), (3), or (4) below, and each of n1 and n2 independently represents an integer of 1 to 10:

[Chemical formula 2]

Formula (2)

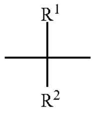

Formula (3)

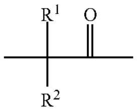

Formula (4)

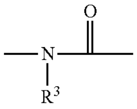

wherein, in formulae (2), (3), and (4), each of $R^1$ and $R^2$ independently represents a hydrogen atom, an alkyl group having 1 to 10 carbon atoms and being optionally interrupted by an oxygen atom or a sulfur atom, an alkenyl group having 2 to 10 carbon atoms and being optionally interrupted by an oxygen atom or a sulfur atom, an alkynyl group having 2 to 10 carbon atoms and being optionally interrupted by an oxygen atom or a sulfur atom, a benzyl group, or a phenyl group, wherein the phenyl group is optionally substituted with at least one monovalent functional group selected from the group consisting of an alkyl group having 1 to 6 carbon atoms, a halogen atom, an alkoxy group having 1 to 10 carbon atoms, a nitro group, a cyano group, and an alkylthio group having 1 to 6 carbon atoms, and $R^3$ represents a hydrogen atom, an alkyl group having 1 to 10 carbon atoms and being optionally interrupted by an oxygen atom or a sulfur atom, an alkenyl group having 3 to 10 carbon atoms and being optionally interrupted by an oxygen atom or a sulfur atom, an alkynyl group having 3 to 10 carbon atoms and being optionally interrupted by an oxygen atom or a sulfur atom, a benzyl group, or a phenyl group, wherein the phenyl group is optionally substituted with at least one monovalent functional group selected from the group consisting of an alkyl group having 1 to 6 carbon atoms, a halogen atom, an alkoxy group having 1 to 10 carbon atoms, a nitro group, a cyano group, an alkylthio group having 1 to 6 carbon atoms, and an organic group represented by the following formula (5):

[Chemical formula 3]

Formula (5)

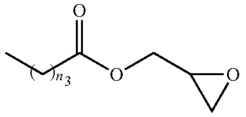

wherein, in formula (5), n3 represents an integer of 1 to 10.

[2] The compound according to [1], wherein, in formula (1), X is represented by formula (4).

[3] The compound according to [2], wherein, in formula (1), n1 and n2 are 1, and $R^3$ is an alkyl group having 1 to 5 carbon atoms and being optionally interrupted by an oxygen atom, or is represented by formula (5).

[4] A resist underlying film-forming composition comprising a solvent, and an epoxy addition product, which is a reaction product of the compound according to any one of [1] to [3] and an epoxy addition product-forming compound.

[5] The resist underlying film-forming composition according to [4], wherein the epoxy addition product-forming compound is at least one compound selected from the group consisting of a carboxylic acid-containing compound, a carboxylic anhydride-containing compound, a hydroxy group-containing compound, a thiol group-containing compound, an amino group-containing compound, and an imide group-containing compound.

[6] The resist underlying film-forming composition according to [4] or [5], wherein the epoxy addition product-forming compound is a carboxylic acid-containing compound or a thiol group-containing compound.

[7] The resist underlying film-forming composition according to [6], wherein the carboxylic acid-containing compound is a dicarboxylic acid having at least one sulfur atom.

[8] The resist underlying film-forming composition according to [7], wherein the dicarboxylic acid having at least one sulfur atom is an aliphatic dicarboxylic acid.

[9] The resist underlying film-forming composition according to any one of [4] to [8], further comprising a crosslinking catalyst.

[10] The resist underlying film-forming composition according to any one of [4] to [9], further comprising a crosslinking agent.

[11] The resist underlying film-forming composition according to any one of [4] to [10], further comprising a surfactant.

[12] A resist underlying film which is a baked product of an applied film comprising the resist underlying film-forming composition according to any one of [4] to [11].

[13] A method for producing a patterned substrate, comprising the steps of: applying the resist underlying film-forming composition according to any one of [4] to [11] onto a semiconductor substrate and baking the applied composition to form a resist underlying film; applying a resist onto the resist underlying film and baking the applied resist to form a resist film; subjecting the semiconductor substrate covered with the resist underlying film and the resist to exposure; and subjecting the exposed resist film to development to perform patterning.

[14] A method for producing a semiconductor device, comprising the steps of:

forming a resist underlying film comprising the resist underlying film-forming composition according to any one of [4] to on a semiconductor substrate;

forming a resist film on the resist underlying film;

irradiating the resist film with a light or an electron beam and subjecting the resultant resist film to development to form a resist pattern;

etching the resist underlying film through the formed resist pattern to form a patterned resist underlying film; and processing the semiconductor substrate using the patterned resist underlying film.

Advantageous Effects of Invention

The resist underlying film-forming composition of the present invention is advantageous in that the formed film has a high dry etching rate and can solve various problems caused due to the reduction of the thickness of a resist film, making it possible to achieve finer microfabrication of a semiconductor substrate.

DESCRIPTION OF EMBODIMENTS

<Compound>

The compound used in the present invention, preferably the epoxy compound for forming an epoxy addition product to be contained in a resist underlying film-forming composition is a compound represented by the following formula (1):

[Chemical formula 4]

Formula (1)

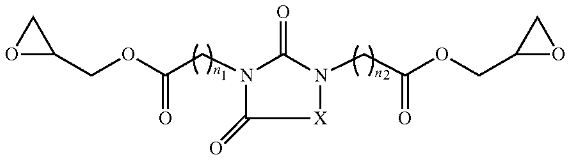

wherein, in formula (1), X is a divalent organic group represented by formula (2), (3), or (4) below, and each of n1 and n2 independently represents an integer of 1 to 10:

[Chemical formula 5]

Formula (2)

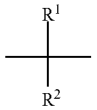

Formula (3)

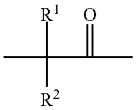

Formula (4)

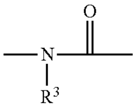

wherein, in formulae (2), (3), and (4), each of $R^1$ and $R^2$ independently represents a hydrogen atom, an alkyl group having 1 to 10 carbon atoms and being optionally interrupted by an oxygen atom or a sulfur atom, an alkenyl group having 2 to 10 carbon atoms and being optionally interrupted by an oxygen atom or a sulfur atom, an alkynyl group having 2 to 10 carbon atoms and being optionally interrupted by an oxygen atom or a sulfur atom, a benzyl group, or a phenyl group, wherein the phenyl group is optionally substituted with at least one monovalent functional group selected from the group consisting of an alkyl group having 1 to 6 carbon atoms, a halogen atom, an alkoxy group having 1 to 6 carbon atoms, a nitro group, a cyano group, and an alkylthio group having 1 to 6 carbon atoms, and $R^3$ represents a hydrogen atom, an alkyl group having 1 to 10 carbon atoms and being optionally interrupted by an oxygen atom or a sulfur atom, an alkenyl group having 2 to 10 carbon atoms and being optionally interrupted by an oxygen atom or a sulfur atom, an alkynyl group having 2 to 10 carbon atoms and being optionally interrupted by an oxygen atom or a sulfur atom, a benzyl group, or a phenyl group, wherein the phenyl group is optionally substituted with at least one monovalent functional group selected from the group consisting of an alkyl group having 1 to 6 carbon atoms, a halogen atom, an alkoxy group having 1 to 6 carbon atoms, a nitro group, a cyano group, an alkylthio group having 1 to 6 carbon atoms, and an organic group represented by the following formula (5):

[Chemical formula 6]

Formula (5)

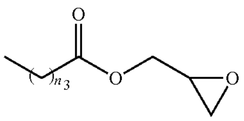

wherein, in formula (5), n3 represents an integer of 1 to 10.

Examples of alkyl groups having 1 to 10 carbon atoms include a methyl group, an ethyl group, a n-propyl group, an i-propyl group, a cyclopropyl group, a n-butyl group, an i-butyl group, a s-butyl group, a t-butyl group, a cyclobutyl group, a 1-methyl-cyclopropyl group, a 2-methyl-cyclopropyl group, a n-pentyl group, a 1-methyl-n-butyl group, a 2-methyl-n-butyl group, a 3-methyl-n-butyl group, a 1,1-dimethyl-n-propyl group, a 1,2-dimethyl-n-propyl group, a 2,2-dimethyl-n-propyl group, a 1-ethyl-n-propyl group, a cyclopentyl group, a 1-methyl-cyclobutyl group, a 2-methyl-cyclobutyl group, a 3-methyl-cyclobutyl group, a 1,2-dimethyl-cyclopropyl group, a 2,3-dimethyl-cyclopropyl group, a 1-ethyl-cyclopropyl group, a 2-ethyl-cyclopropyl group, a n-hexyl group, a 1-methyl-n-pentyl group, a 2-methyl-n-pentyl group, a 3-methyl-n-pentyl group, a 4-methyl-n-pentyl group, a 1,1-dimethyl-n-butyl group, a 1,2-dimethyl-n-butyl group, a 1,3-dimethyl-n-butyl group, a 2,2-dimethyl-n-butyl group, a 2,3-dimethyl-n-butyl group, a 3,3-dimethyl-n-butyl group, a 1-ethyl-n-butyl group, a 2-ethyl-n-butyl group, a 1,1,2-trimethyl-n-propyl group, a 1,2,2-trimethyl-n-propyl group, a 1-ethyl-1-methyl-n-propyl group, a 1-ethyl-2-methyl-n-propyl group, a cyclohexyl group, a 1-methyl-cyclopentyl group, a 2-methyl-cyclopentyl group, a 3-methyl-cyclopentyl group, a 1-ethyl-cyclobutyl group, a 2-ethyl-cyclobutyl group, a 3-ethyl-cyclobutyl group, a 1,2-dimethyl-cyclobutyl group, a 1,3-dimethyl-cyclobutyl group, a 2,2-dimethyl-cyclobutyl group, a 2,3-dimethyl-cyclobutyl group, a 2,4-dimethyl-cyclobutyl group, a 3,3-dimethyl-cyclobutyl group, a 1-n-propyl-cyclopropyl group, a 2-n-propyl-cyclopropyl group, a 1-i-propyl-cyclopropyl group, a 2-i-propyl-cyclopropyl group, a 1,2,2-trimethyl-cyclopropyl group, a 1,2,3-trimethyl-cyclopropyl group, a 2,2,3-trimethyl-cyclopropyl group, a 1-ethyl-2-methyl-cyclopropyl group, a 2-ethyl-1-methyl-cyclopropyl group, a 2-ethyl-2-methyl-cyclopropyl group, and a 2-ethyl-3-methyl-cyclopropyl group.

Examples of alkenyl groups having 2 to 10 carbon atoms include an ethenyl group, a 1-propenyl group, a 2-propenyl group, a 1-methyl-1-ethenyl group, a 1-butenyl group, a 2-butenyl group, a 3-butenyl group, a 2-methyl-1-propenyl group, a 2-methyl-2-propenyl group, a 1-ethylethenyl group, a 1-methyl-1-propenyl group, a 1-methyl-2-propenyl group, a 1-pentenyl group, a 2-pentenyl group, a 3-pentenyl group, a 4-pentenyl group, a 1-n-propylethenyl group, a 1-methyl-1-butenyl group, a 1-methyl-2-butenyl group, a 1-methyl-3-butenyl group, a 2-ethyl-2-propenyl group, a 2-methyl-1-butenyl group, a 2-methyl-2-butenyl group, a 2-methyl-3-butenyl group, a 3-methyl-1-butenyl group, a 3-methyl-2-butenyl group, a 3-methyl-3-butenyl group, a 1,1-dimethyl-2-propenyl group, a 1-i-propylethenyl group, a 1,2- dimethyl-1-propenyl group, a 1,2-dimethyl-2-propenyl group, a 1-cyclopentenyl group, a 2-cyclopentenyl group, a 3-cyclopentenyl group, a 1-hexenyl group, a 2-hexenyl group, a 3-hexenyl group, a 4-hexenyl group, 5-hexenyl group, a 1-methyl-1-pentenyl group, a 1-methyl-2-pentenyl group, a 1-methyl-3-pentenyl group, a 1-methyl-4-pentenyl group, a 1-n-butylethenyl group, a 2-methyl-1-pentenyl group, a 2-methyl-2-pentenyl group, a 2-methyl-3-pentenyl group, a 2-methyl-4-pentenyl group, a 2-n-propyl-2-propenyl group, a 3-methyl-1-pentenyl group, a 3-methyl-2-pentenyl group, a 3-methyl-3-pentenyl group, a 3-methyl-4-pentenyl group, a 3-ethyl-3-butenyl group, a 4-methyl-1-pentenyl group, a 4-methyl-2-pentenyl group, a 4-methyl-3-pentenyl group, a 4-methyl-4-pentenyl group, a 1,1-dimethyl-2-butenyl group, a 1,1-dimethyl-3-butenyl group, a 1,2-dimethyl-1-butenyl group, a 1,2-dimethyl-2-butenyl group, a 1,2-dimethyl-3-butenyl group, a 1-methyl-2-ethyl-2-propenyl group, a 1-s-butylethenyl group, a 1,3-dimethyl-1-butenyl group, a 1,3-dimethyl-2-butenyl group, a 1,3-dimethyl-3-butenyl group, a 1-i-butylethenyl group, a 2,2-dimethyl-3-butenyl group, a 2,3-dimethyl-1-butenyl group, a 2,3-dimethyl-2-butenyl group, a 2,3-dimethyl-3-butenyl group, a 2-i-propyl-2-propenyl group, a 3,3-dimethyl-1-butenyl group, a 1-ethyl-1-butenyl group, a 1-ethyl-2-butenyl group, a 1-ethyl-3-butenyl group, a 1-n-propyl-1-propenyl group, a 1-n-propyl-2-propenyl group, a 2-ethyl-1-butenyl group, a 2-ethyl-2-butenyl group, a 2-ethyl-3-butenyl group, a 1,1,2-trimethyl-2-propenyl group, a 1-t-butylethenyl group, a 1-methyl-1-ethyl-2-propenyl group, a 1-ethyl-2-methyl-1-propenyl group, a 1-ethyl-2-methyl-2-propenyl group, a 1-i-propyl-1-propenyl group, a 1-i-propyl-2-propenyl group, a 1-methyl-2-cyclopentenyl group, a 1-methyl-3-cyclopentenyl group, a 2-methyl-1-cyclopentenyl group, a 2-methyl-2-cyclopentenyl group, a 2-methyl-3-cyclopentenyl group, a 2-methyl-4-cyclopentenyl group, a 2-methyl-5-cyclopentenyl group, a 2-methylene-cyclopentyl group, a 3-methyl-1-cyclopentenyl group, a 3-methyl-2-cyclopentenyl group, a 3-methyl-3-cyclopentenyl group, a 3-methyl-4-cyclopentenyl group, a 3-methyl-5-cyclopentenyl group, a 3-methylene-cyclopentyl group, a 1-cyclohexenyl group, a 2-cyclohexenyl group, and a 3-cyclohexenyl group.

Examples of alkynyl groups having 2 to 10 carbon atoms include an ethynyl group, a 1-propynyl group, a 2-propynyl group, a 1-butynyl group, a 2-butynyl group, a 3-butynyl group, a 4-methyl-1-pentynyl group, and a 3-methyl-1-pentynyl group.

The language "being optionally interrupted by an oxygen atom or a sulfur atom" means that a carbon atom in, for example, the above-mentioned alkyl group, alkenyl group, or alkynyl group may be replaced with an oxygen atom or a sulfur atom. For example, replacement of a carbon atom in the alkyl group, alkenyl group, or alkynyl group with an oxygen atom results in a compound having an ether linkage, and, for example, replacement of a carbon atom in the alkyl group, alkenyl group, or alkynyl group with a sulfur atom results in a compound having a thioether linkage.

Examples of alkyl groups having 1 to 6 carbon atoms include alkyl groups having 1 to 6 carbon atoms among the above-mentioned alkyl groups having 1 to 10 carbon atoms.

Examples of halogen atoms include fluorine, chlorine, bromine, and iodine.

Examples of alkoxy groups having 1 to 10 carbon atoms include a methoxy group, an ethoxy group, a n-propoxy group, an i-propoxy group, a n-butoxy group, an i-butoxy group, a s-butoxy group, a t-butoxy group, a n-pentoxy group, a 1-methyl-n-butoxy group, a 2-methyl-n-butoxy group, a 3-methyl-n-butoxy group, a 1,1-dimethyl-n-propoxy group, a 1,2-dimethyl-n-propoxy group, a 2,2-dimethyl-n-propoxy group, a 1-ethyl-n-propoxy group, a n-hexyloxy group, a 1-methyl-n-pentyloxy group, a 2-methyl-n-pentyloxy group, a 3-methyl-n-pentyloxy group, a 4-methyl-n-pentyloxy group, a 1,1-dimethyl-n-butoxy group, a 1,2-dimethyl-n-butoxy group, a 1,3-dimethyl-n-butoxy group, a 2,2-dimethyl-n-butoxy group, a 2,3-dimethyl-n-butoxy group, a 3,3-dimethyl-n-butoxy group, a 1-ethyl-n-butoxy group, a 2-ethyl-n-butoxy group, a 1,1,2-trimethyl-n-propoxy group, a 1,2,2,-trimethyl-n-propoxy group, a 1-ethyl-1-methyl-n-propoxy group, and a 1-ethyl-2-methyl-n-propoxy group.

Examples of alkylthio groups having 1 to 6 carbon atoms include an ethylthio group, a butylthio group, and a hexylthio group.

It is preferred that, in formula (1), X is represented by formula (4).

It is preferred that, in formula (1), X is represented by formula (4), n1 and n2 are 1, and $R^3$ is an alkyl group having 1 to 5 carbon atoms and being optionally interrupted by an oxygen atom. In this case, specific examples of the alkyl group having 1 to 5 carbon atoms include alkyl groups having 1 to 5 carbon atoms among the above-mentioned alkyl groups having 1 to 10 carbon atoms.

Preferred is a compound of formula (1) wherein X is represented by formula (4), n1 and n2 are 1, $R^3$ is a methyl group, a methoxymethyl group, or represented by formula (5), and n3 is 1, that is, a compound represented by the following formula (A-1), (A-7), or (A-19).

[Chemical formula 7]

Formula (A-1)

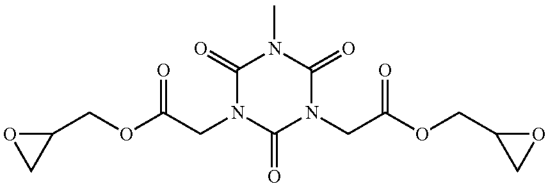

[Chemical formula 8]

Formula (A-7)

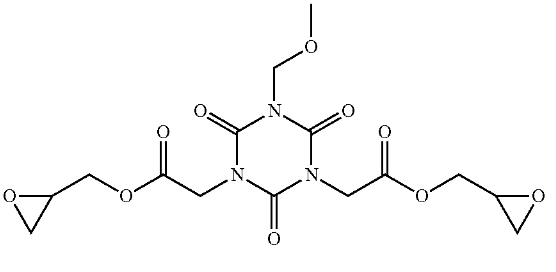

-continued
[Chemical formula 9]
Formula (A-19)
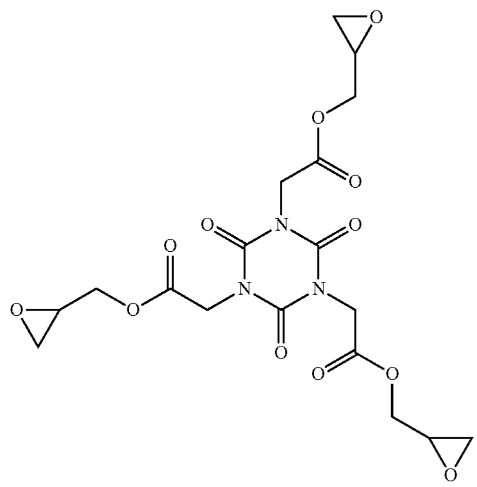
The compound represented by formula (1) in the present invention, for example, includes formulae (A-1) to (A-21) below, but the compound is not limited to these formulae.
[Chemical formula 10]
Formula(A-1)
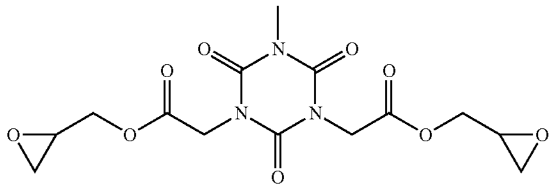
Formula(A-2)
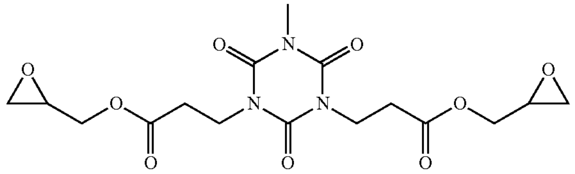
Formula(A-3)
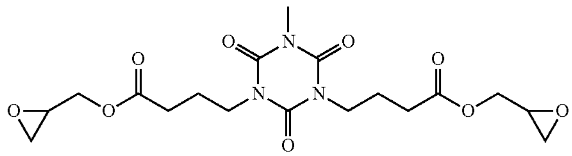
Formula(A-4)
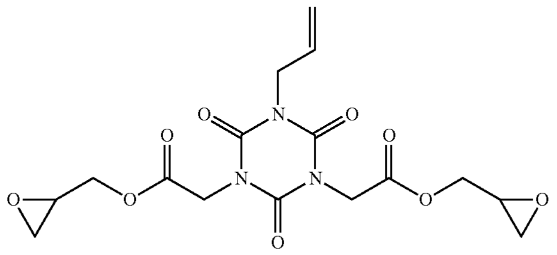
-continued
Formula(A-5)
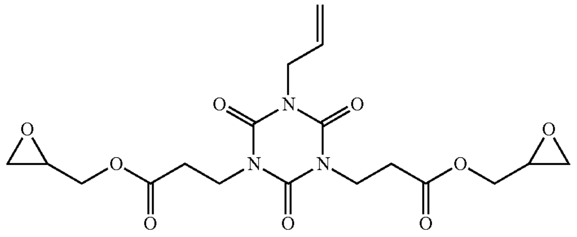
Formula(A-6)
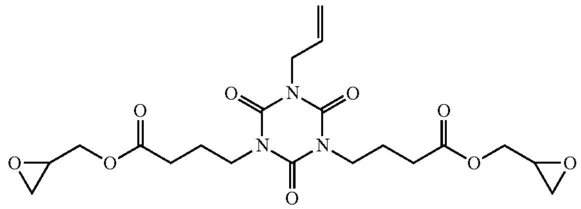
Formula(A-7)
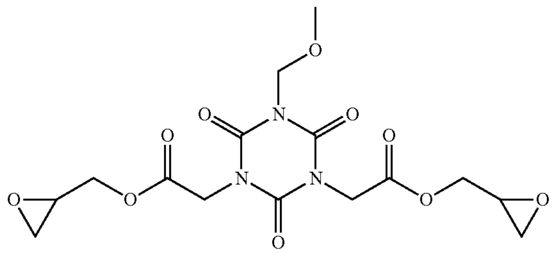
Formula(A-8)
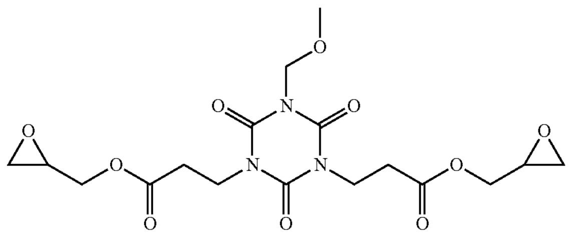
Formula(A-9)
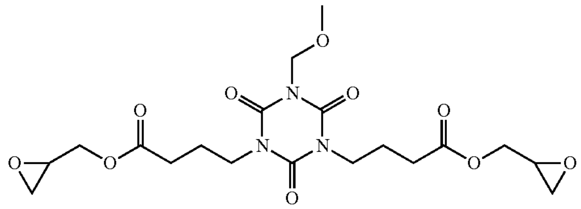
[Chemical formula 11]
Formula(A-10)
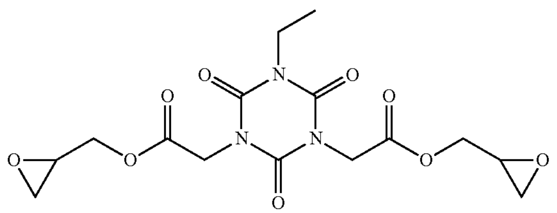

-continued
Formula(A-11)
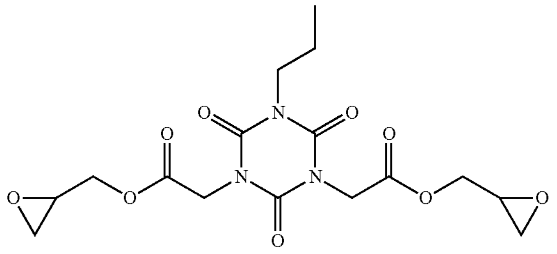
Formula(A-12)
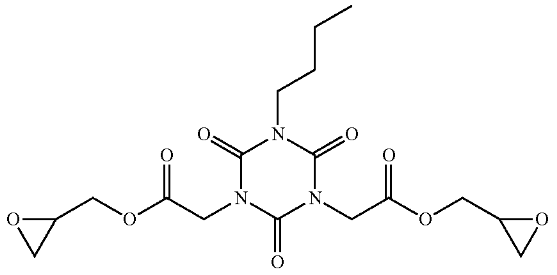
Formula(A-13)
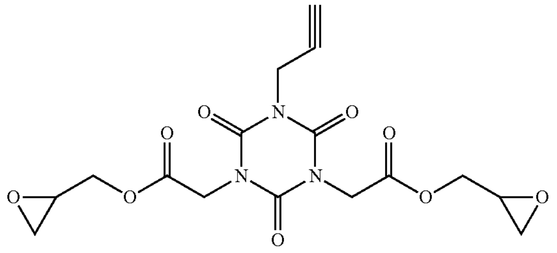
Formula(A-14)
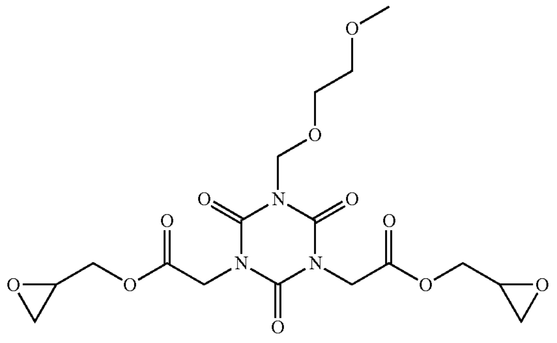
-continued
Formula(A-15)
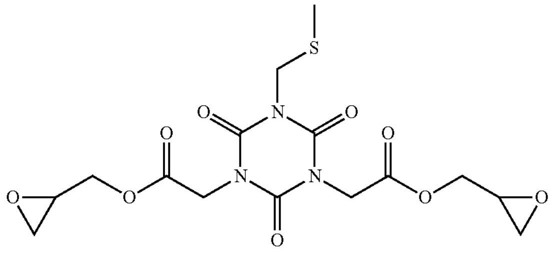
Formula(A-16)
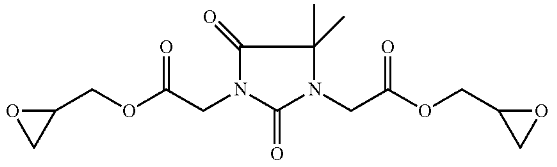
Formula(A-17)
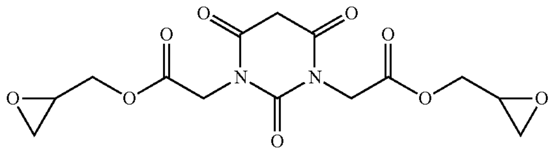
Formula(A-18)
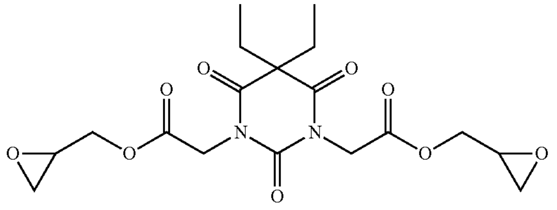
[Chemical formula 12]
Formula(A-19)
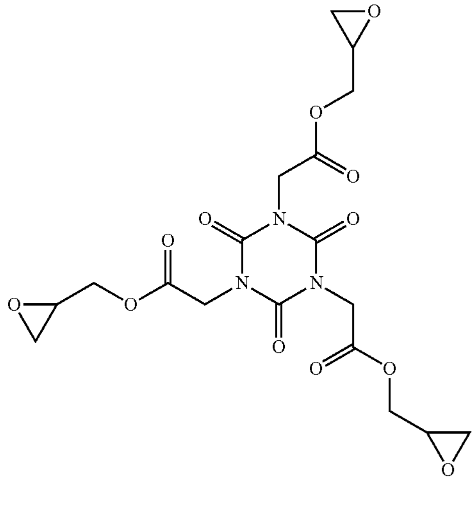

-continued

Formula(A-20)

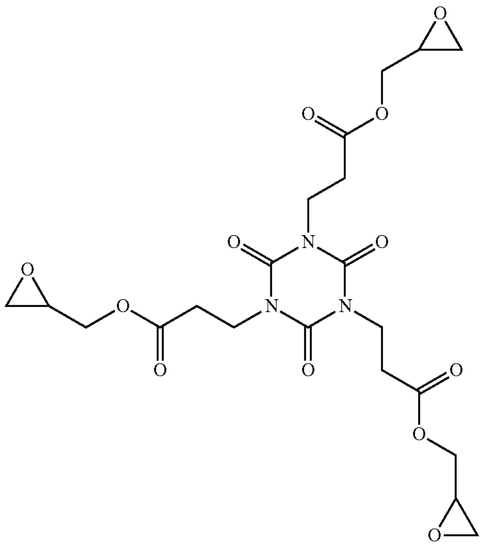

Formula(A-21)

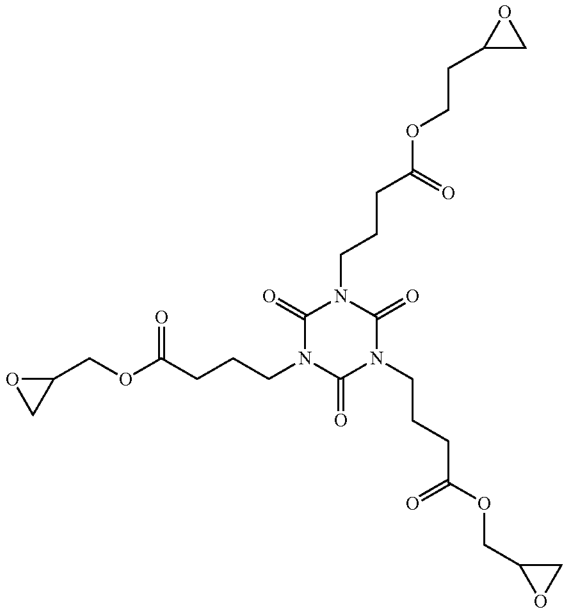

<Epoxy Addition Product and Epoxy Addition Product-Forming Compound>

The epoxy addition product in the present invention may be formed by addition of an epoxy addition product-forming compound, such as a carboxylic acid-containing compound, a carboxylic anhydride-containing compound, a hydroxy group-containing compound, a thiol group-containing compound, an amino group-containing compound, or an imide group-containing compound, to the epoxy compound represented by formula (1) above by a method known per se.

The epoxy addition product-forming compound in the present invention, for example, includes formulae (B-1) to (B-53) below, but the compound is not limited to these formulae.

[Chemical formula 13]

Formula(B-1)

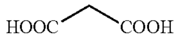

Formula(B-2)

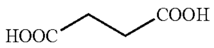

Formula(B-3)

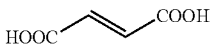

Formula(B-4)

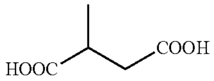

Formula(B-5)

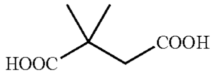

Formula(B-6)

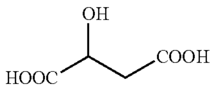

Formula(B-7)

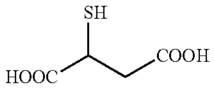

Formula(B-8)

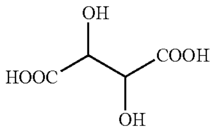

Formula(B-9)

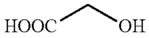

Formula(B-10)

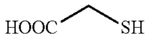

Formula(B-11)

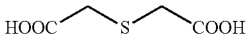

Formula(B-12)

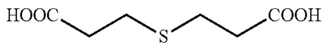

Formula(B-13)

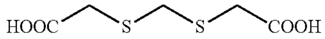

Formula(B-14)

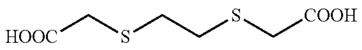

Formula(B-15)

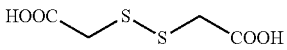

Formula(B-16)

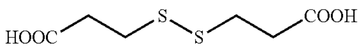

Formula(B-17)

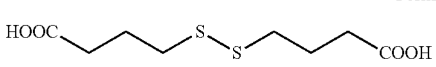

[Chemical formula 14]

Formula(B-18)

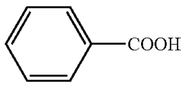

Formula(B-19)

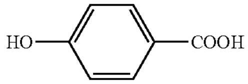

-continued
Formula(B-20)
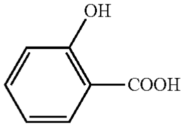
Formula(B-21)
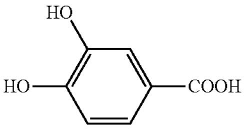
Formula(B-22)
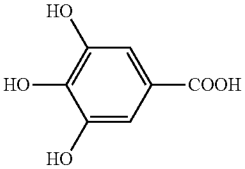
Formula(B-23)
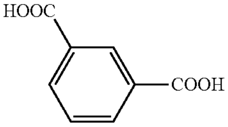
Formula(B-24)
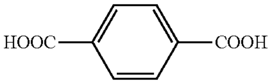
Formula(B-25)
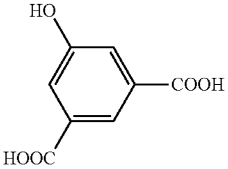
Formula(B-26)
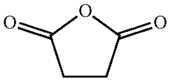
Formula(B-27)
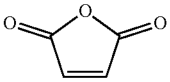
Formula(B-28)
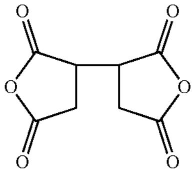
Formula(B-29)
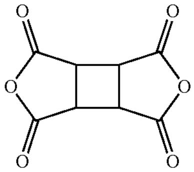
[Chemical formula 15]
Formula(B-30)
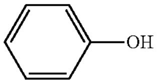
-continued
Formula(B-31)
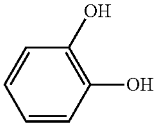
Formula(B-32)
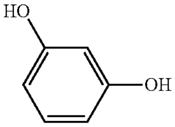
Formula(B-33)
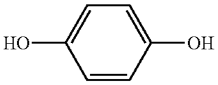
Formula(B-34)
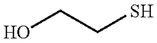
Formula(B-35)
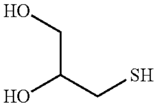
Formula(B-36)
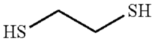
Formula(B-37)
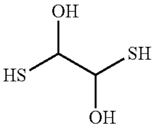
Formula(B-38)
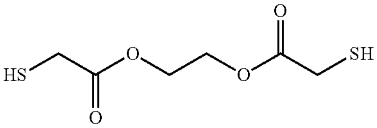
Formula(B-39)
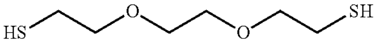
Formula(B-40)
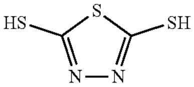
Formula(B-41)
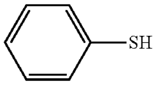
Formula(B-42)
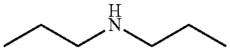
Formula(B-43)
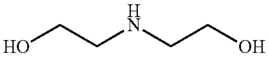
[Chemical formula 16]
Formula(B-44)
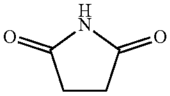
Formula(B-45)
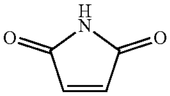

-continued

Formula(B-46)

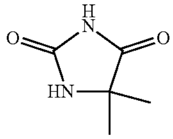

Formula(B-47)

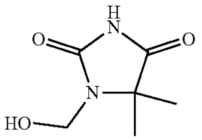

Formula(B-48)

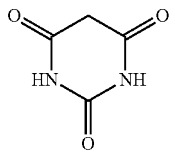

Formula(B-49)

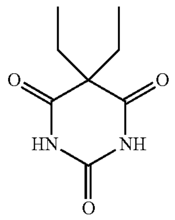

Formula(B-50)

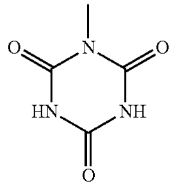

Formula(B-51)

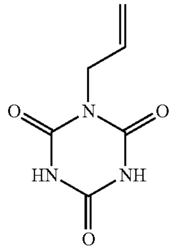

Formula(B-52)

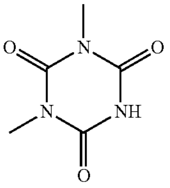

Formula(B-53)

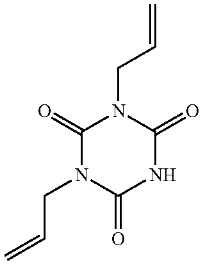

Of these epoxy addition product-forming compounds, a carboxylic acid-containing compound (for example, formulae (B-1) to (B-25) above) or a thiol group-containing compound (for example, formulae (B-7), (B-10), and (B-34) to (B-41) above) is preferred.

The carboxylic acid-containing compound is preferably a dicarboxylic acid having at least one sulfur atom (for example, formulae (B-7) and (B-11) to (B-17) above).

The dicarboxylic acid having at least one sulfur atom is preferably an aliphatic dicarboxylic acid, especially preferably dithioglycolic acid (formula (B-15)).

The molar ratio of the compound represented by formula (1) above and the epoxy addition product-forming compound during the reaction is within the range of, for example, 1:0.1-10, preferably 1:1-5, more preferably 1:1-3.

The epoxy addition product in the present invention has a weight average molecular weight of, for example, 1,000 to 100,000, or 1,100 to 50,000, or 1,200 to 30,000, or 1,300 to 20,000.

[Solvent]

The resist underlying film-forming composition of the present invention may be produced by dissolving the above-mentioned components in an organic solvent, and is used in a uniform solution state.

With respect to the solvent for the resist underlying film-forming composition of the present invention, there is no particular limitation as long as it is a solvent that can dissolve therein the above-mentioned compounds or reaction product thereof, and any of such solvents may be used. Particularly, because the resist underlying film-forming composition of the present invention is used in a uniform solution state, it is recommendable to use a solvent usually used in a lithography process in combination, in view of the coatability of the composition.

Examples of the organic solvents include ethylene glycol monomethyl ether, ethylene glycol monoethyl ether, methyl cellosolve acetate, ethyl cellosolve acetate, diethylene glycol monomethyl ether, diethylene glycol monoethyl ether, propylene glycol, propylene glycol monomethyl ether, propylene glycol monoethyl ether, propylene glycol monomethyl ether acetate, propylene glycol propyl ether acetate, toluene, xylene, methyl ethyl ketone, methyl isobutyl ketone, cyclopentanone, cyclohexanone, cycloheptanone, 4-methyl-2-pentanol, methyl 2-hydroxyisobutyrate, ethyl 2-hydroxyisobutyrate, ethyl ethoxyacetate, 2-hydroxyethyl acetate, methyl 3-methoxypropionate, ethyl 3-methoxypropionate, ethyl 3-ethoxypropionate, methyl 3-ethoxypropionate, methyl pyruvate, ethyl pyruvate, ethyl acetate, butyl acetate, ethyl lactate, butyl lactate, 2-heptanone, methoxycyclopentane, anisole, γ-butyrolactone, N-methylpyrrolidone, N,N-dimethylformamide, and N,N-dimethylacetamide. These solvents may be used each alone or in combination.

Of these solvents, for example, propylene glycol monomethyl ether, propylene glycol monomethyl ether acetate, ethyl lactate, butyl lactate, and cyclohexanone are preferred. Especially preferred are propylene glycol monomethyl ether and propylene glycol monomethyl ether acetate.

[Crosslinking Catalyst]

The resist underlying film-forming composition of the present invention may contain, as an optional component, a crosslinking catalyst for accelerating the crosslinking reaction. As the crosslinking catalyst, an acidic compound, a basic compound, or a compound capable of generating an acid or a base due to heat may be used. As the acidic compound, a sulfonic acid compound or a carboxylic acid compound may be used. And, as the compound capable of generating an acid due to heat, a thermal acid generator may be used.

Examples of sulfonic acid compounds or carboxylic acid compounds include p-toluenesulfonic acid, trifluoromethanesulfonic acid, pyridinium trifluoromethanesulfonate, pyridinium p-toluenesulfonate, salicylic acid, camphorsulfonic acid, 5-sulfosalicylic acid, 4-chlorobenzenesulfonic acid, 4-hydroxybenzenesulfonic acid, pyridinium 4-hydroxybenzenesulfonate, benzenedisulfonic acid, 1-naphthalenesulfonic acid, 4-nitrobenzenesulfonic acid, citric acid, benzoic acid, and hydroxybenzoic acid.

Examples of thermal acid generators include K-PURE [registered trademark] CXC-1612, K-PURE CXC-1614, K-PURE TAG-2172, K-PURE TAG-2179, K-PURE TAG-2678, K-PURE TAG2689 (each of which is manufactured by King Industries, Inc.), and SI-45, SI-60, SI-80, SI-100, SI-110, SI-150 (each of which is manufactured by Sanshin Chemical Industry Co., Ltd.).

These crosslinking catalysts may be used each alone or in combination. Further, as the basic compound, an amine compound or an ammonium hydroxide compound may be used. And, as the compound capable of generating a base due to heat, urea may be used.

Examples of amine compounds include tertiary amines, such as triethanolamine, tributanolamine, trimethylamine, triethylamine, trinormalpropylamine, triisopropylamine, trinormalbutylamine, tri-tert-butylamine, trinormaloctylamine, triisopropanolamine, phenyldiethanolamine, stearyldiethanolamine, and diazabicyclooctane, and aromatic amines, such as pyridine and 4-dimethylaminopyridine. Further examples of amine compounds include primary amines, such as benzylamine and normalbutylamine, and secondary amines, such as diethylamine and dinormalbutylamine. These amine compounds may be used each alone or in combination.

Examples of ammonium hydroxide compounds include tetramethylammonium hydroxide, tetraethylammonium hydroxide, tetrapropylammonium hydroxide, tetrabutylammonium hydroxide, benzyltrimethylammonium hydroxide, benzyltriethylammonium hydroxide, cetyltrimethylammonium hydroxide, phenyltrimethylammonium hydroxide, and phenyltrimethylammonium hydroxide.

As the compound capable of generating a base due to heat, for example, a compound, which has a thermally unstable group, such as an amide group, an urethane group, or an aziridine group, and generates an amine upon being heated, may be used. Further examples of the compounds capable of generating a base due to heat include urea, benzyltrimethylammonium chloride, benzyltriethylammonium chloride, benzyldimethylphenylammonium chloride, benzyldodecyldimethylammonium chloride, benzyltributylammonium chloride, and choline chloride.

When the resist underlying film-forming composition contains a crosslinking catalyst, it contains the catalyst in an amount of 0.0001 to 20% by mass, preferably 0.01 to 15% by mass, more preferably 0.1 to 10% by mass, based on the total mass of the solid components in the resist underlying film-forming composition.

Among the above-mentioned compounds, an acidic compound and/or a compound capable of generating an acid due to heat (crosslinking acid catalyst) is preferred.

[Crosslinking Agent]

The resist underlying film-forming composition of the present invention may contain a crosslinking agent. Examples of the crosslinking agent include melamine-type, substituted urea-type, or their polymer-type ones. Preferred is a crosslinking agent having at least two crosslinkable substituents, and examples thereof include methoxymethylated glycoluril, butoxymethylated glycoluril, methoxymethylated melamine, butoxymethylated melamine, methoxymethylated benzoguanamine, butoxymethylated benzoguanamine, methoxymethylated urea, butoxymethylated urea, methoxymethylated thiourea, and methoxymethylated thiourea. Further, condensation products of these compounds may also be used.

As the crosslinking agent, a crosslinking agent having a high heat resistance may be used. As such a crosslinking agent having a high heat resistance, a compound containing in the molecule thereof a crosslinkable substituent having an aromatic ring (for example, a benzene ring or a naphthalene ring) may be used.

Examples of such a compound include compounds having a partial structure of formula (5-1) below, and polymers or oligomers having a repeating unit of formula (5-2) below.

[Chemical formula 17]

Formula (5-1)

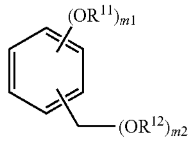

Formula (5-2)

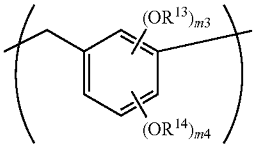

$R^{11}$, $R^{12}$, $R^{13}$, and $R^{14}$ above are a hydrogen atom or an alkyl group having 1 to 10 carbon atoms. m1, m2, m3, and m4 each represent an integer of 0 to 3. Examples of alkyl groups having 1 to 10 carbon atoms include a methyl group, an ethyl group, a n-propyl group, an i-propyl group, a cyclopropyl group, a n-butyl group, an i-butyl group, a s-butyl group, a t-butyl group, a cyclobutyl group, a 1-methyl-cyclopropyl group, a 2-methyl-cyclopropyl group, a n-pentyl group, a 1-methyl-n-butyl group, a 2-methyl-n-butyl group, a 3-methyl-n-butyl group, a 1,1-dimethyl-n-propyl group, a 1,2-dimethyl-n-propyl group, a 2,2-dimethyl-n-propyl group, a 1-ethyl-n-propyl group, a cyclopentyl group, a 1-methyl-cyclobutyl group, a 2-methyl-cyclobutyl group, a 3-methyl-cyclobutyl group, a 1,2-dimethyl-cyclopropyl group, a 2,3-dimethyl-cyclopropyl group, a 1-ethyl-cyclopropyl group, a 2-ethyl-cyclopropyl group, a n-hexyl group, a 1-methyl-n-pentyl group, a 2-methyl-n-pentyl group, a 3-methyl-n-pentyl group, a 4-methyl-n-pentyl group, a 1,1-dimethyl-n-butyl group, a 1,2-dimethyl-n-butyl group, a 1,3-dimethyl-n-butyl group, a 2,2-dimethyl-n-butyl group, a 2,3-dimethyl-n-butyl group, a 3,3-dimethyl-n-butyl group, a 1-ethyl-n-butyl group, a 2-ethyl-n-butyl group, a 1,1,2-trimethyl-n-propyl group, a 1,2,2-trimethyl-n-propyl group, a 1-ethyl-1-methyl-n-propyl group, a 1-ethyl-2-methyl-n-propyl group, a cyclohexyl group, a 1-methyl-cyclopentyl group, a 2-methyl-cyclopentyl group, a 3-methyl-cyclopentyl group, a 1-ethyl-cyclobutyl group, a 2-ethyl-cyclobutyl group, a 3-ethyl-cyclobutyl group, a 1,2-dimethyl-cyclobutyl group, a 1,3-dimethyl-cyclobutyl group, a 2,2-dimethyl-cyclobutyl group, a 2,3-dimethyl-cyclobutyl group, a 2,4-dimethylcyclobutyl group, a 3,3-dimethyl-cyclobutyl group, a 1-n-propyl-cyclopropyl group, a 2-n-propyl-cyclopropyl group, a 1-i-propyl-cyclopropyl group, a 2-i-propyl-cyclopropyl group, a 1,2,2-trimethyl-cyclopropyl group, a 1,2,3-trimethyl-cyclopropyl group, a 2,2,3-trimethyl-cyclopropyl group, a 1-ethyl-2-methyl-cyclopropyl group, a 2-ethyl-1-methyl-cyclopropyl group, a 2-ethyl-2-methyl-cyclopropyl group, and a 2-ethyl-3-methyl-cyclopropyl group.

m1 satisfies the inequality: $1 \leq m1 \leq 6-m2$; m2 satisfies the inequality: $1 \leq m2 \leq 5$; m3 satisfies the inequality: $1 \leq m3 \leq 4-m2$; and m4 satisfies the inequality: 1≤m4 10≤3.

Examples of the compounds, polymers, and oligomers of formulae (5-1) and (5-2) are shown below.

[Chemical formula 18]

Formula (6-1)

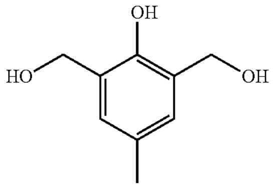

Formula (6-2)

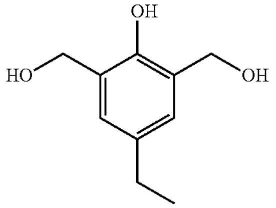

Formula (6-3)

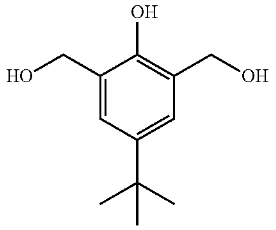

Formula (6-4)

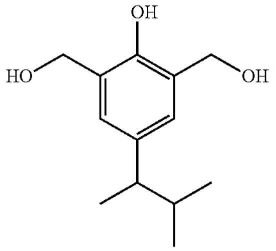

Formula (6-5)

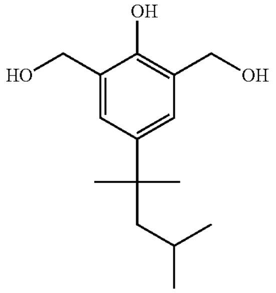

-continued

Formula (6-6)

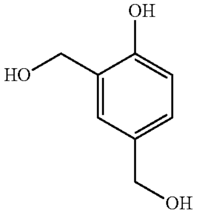

Formula (6-6)

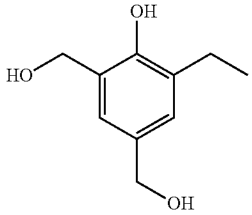

Formula (6-7)

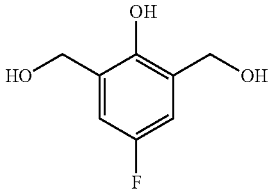

Formula (6-8)

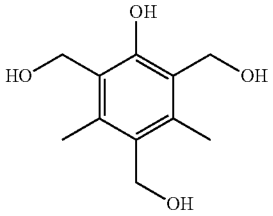

Formula (6-9)

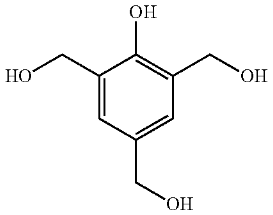

Formula (6-10)

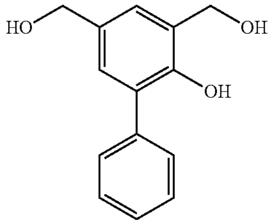

Formula (6-11)

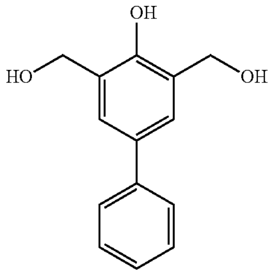

-continued
Formula (6-12)
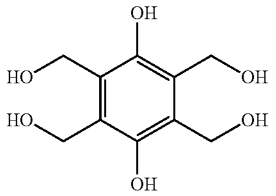
Formula (6-13)
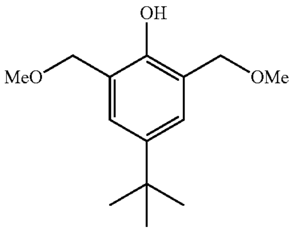
Formula (6-14)
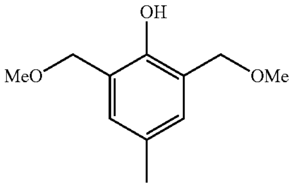
[Chemical formula 19]
Formula (6-15)
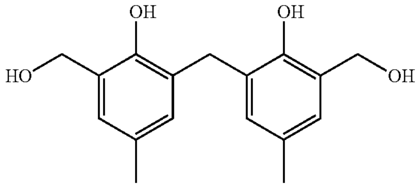
Formula (6-16)
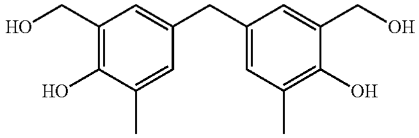
Formula (6-17)
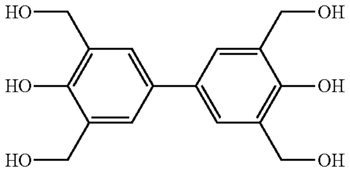
Formula (6-18)
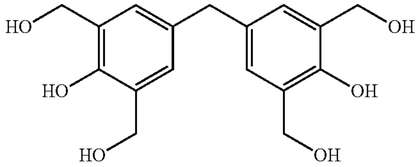
Formula (6-19)
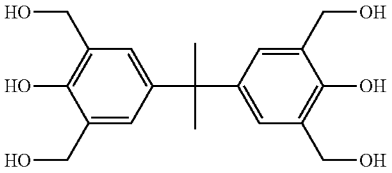
-continued
Formula (6-20)
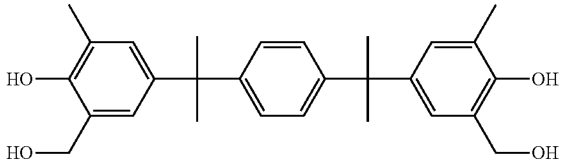
Formula (6-21)
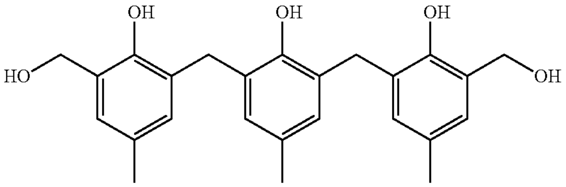
Formula (6-22)
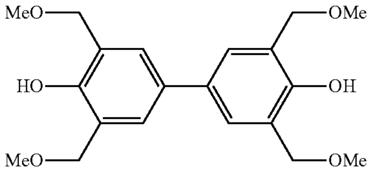
Formula (6-23)
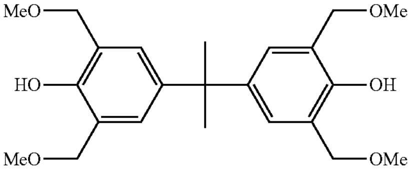
Formula (6-24)
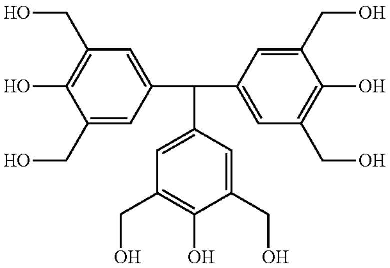
Formula (6-25)
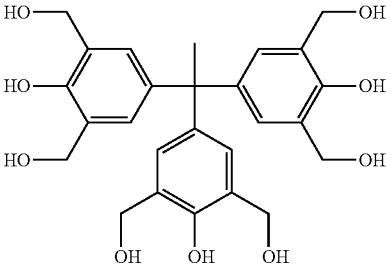

-continued

Formula (6-26)

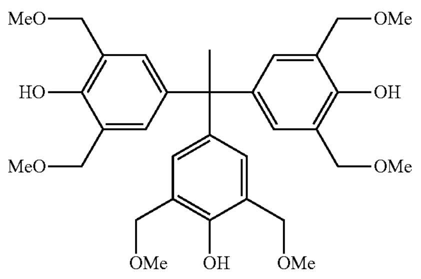

The above-mentioned compounds are available as products of Asahi Yukizai Corporation and Honshu Chemical Industry Co., Ltd. For example, among the above-mentioned crosslinking agents, the compound of formula (6-22) is available under the trade name: TMOM-BP, from Asahi Yukizai Corporation.

The amount of the crosslinking agent added varies depending on, for example, the application solvent used, the substrate used, the required solution viscosity, or the required film form; however, it is within the range of 0.001 to 80% by weight, preferably 0.01 to 50% by weight, more preferably 0.1 to 40% by weight, based on the total weight of the solid components in the resist underlying film-forming composition. The crosslinking agent possibly causes a crosslinking reaction due to self-condensation; however, in the presence of a crosslinkable substituent in the above-mentioned polymer according to the present invention, it may cause a crosslinking reaction with the crosslinkable substituent.

[Surfactant]

The resist underlying film-forming composition of the present invention may contain, as an optional component, a surfactant for improving the coatability to a semiconductor substrate. Examples of the surfactants include nonionic surfactants, e.g., polyoxyethylene alkyl ethers, such as polyoxyethylene lauryl ether, polyoxyethylene stearyl ether, polyoxyethylene cetyl ether, and polyoxyethylene oleyl ether; polyoxyethylene alkyl aryl ethers, such as polyoxyethylene octyl phenyl ether and polyoxyethylene nonyl phenyl ether; polyoxyethylene-polyoxypropylene block copolymers; sorbitan fatty acid esters, such as sorbitan monolaurate, sorbitan monopalmitate, sorbitan monostearate, sorbitan monooleate, sorbitan trioleate, and sorbitan tristearate; and polyoxyethylene sorbitan fatty acid esters, such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate, fluorine surfactants, such as EFTOP [registered trademark] EF301, EFTOP EF303, EFTOP EF352 (manufactured by Mitsubishi Materials Electronic Chemicals Co., Ltd.), MEGAFACE [registered trademark] F171, MEGAFACE F173, MEGAFACE R-30, MEGAFACE R-30N, MEGAFACE R-40, MEGAFACE R-40-LM (manufactured by DIC Corporation), Fluorad FC430, Fluorad FC431 (manufactured by Sumitomo 3M), and AsahiGuard [registered trademark] AG710, Surflon [registered trademark] S-382, Surflon SC101, Surflon SC102, Surflon SC103, Surflon SC104, Surflon SC105, Surflon SC106 (manufactured by AGC Inc.), and organosiloxane polymer KP341 (manufactured by Shin-Etsu Chemical Co., Ltd.). These surfactants may be used each alone or in combination. When the resist underlying film-forming composition contains a surfactant, it contains the surfactant in an amount of 0.0001 to 10% by weight, preferably 0.01 to 5% by weight, based on the total weight of the solid components in the resist underlying film-forming composition.

The resist underlying film-forming composition of the present invention usually has a content of solid components of 0.1 to 70% by mass, preferably 0.1 to 60% by mass. The content of solid components indicates the content of all components left behind the removal of the solvent from the resist underlying film-forming composition. The proportion of the compound or reaction product according to the present invention in the solid components is within the range of 1 to 100% by mass, 1 to 99.9% by mass, 50 to 99.9% by mass, 50 to 95% by mass, and 50 to 90% by mass, with increasing preference.

[Other Components]

In the resist underlying film-forming composition of the present invention, for example, a light absorber, a rheology modifier, or a bonding auxiliary may be added. The rheology modifier is effective in improving the fluidity of the resist underlying film-forming composition. The bonding auxiliary is effective in improving the adhesion between a semiconductor substrate or a resist and the resist underlying film.

With respect to the light absorber, for example, commercially available light absorbers described in “Kougyo-you Shikiso no Gijutsu to Shijou (Techniques and Markets of Industrial Dyes)” (CMC Publishing Co., Ltd.) and “Senryo Binran (Dye Handbook)” (edited by The Society of Synthetic Organic Chemistry, Japan), for example, C. I. Disperse Yellow 1, 3, 4, 5, 7, 8, 13, 23, 31, 49, 50, 51, 54, 60, 64, 66, 68, 79, 82, 88, 90, 93, 102, 114, and 124; C. I. Disperse Orange 1, 5, 13, 25, 29, 30, 31, 44, 57, 72, and 73; C. I. Disperse Red 1, 5, 7, 13, 17, 19, 43, 50, 54, 58, 65, 72, 73, 88, 117, 137, 143, 199, and 210; C. I. Disperse Violet 43; C. I. Disperse Blue 96; C. I. Fluorescent Brightening Agent 112, 135, and 163; C. I. Solvent Orange 2 and 45; C. I. Solvent Red 1, 3, 8, 23, 24, 25, 27, and 49; C. I. Pigment Green 10; and C. I. Pigment Brown 2, may be preferably used. The light absorber is incorporated usually in an amount of 10% by mass or less, preferably 5% by mass or less, based on the total mass of the solid components in the resist underlying film-forming composition.

A rheology modifier is added mainly for the purpose of improving the fluidity of the resist underlying film-forming composition, particularly for improving the uniformity of the thickness of the resist underlying film or the filling of the inside of hole with the resist underlying film-forming composition in the baking step. Specific examples of rheology modifiers include phthalic acid derivatives, such as dimethyl phthalate, diethyl phthalate, diisobutyl phthalate, dihexyl phthalate, and butylisodecyl phthalate; adipic acid derivatives, such as dinormalbutyl adipate, diisobutyl adipate, diisooctyl adipate, and octyldecyl adipate; maleic acid derivatives, such as dinormalbutyl maleate, diethyl maleate, and dinonyl maleate; oleic acid derivatives, such as methyl oleate, butyl oleate, and tetrahydrofurfuryl oleate; and stearic acid derivatives, such as normalbutyl stearate and glyceryl stearate. The rheology modifier is incorporated usually in an amount of less than 30% by mass, based on the total mass of the solid components in the resist underlying film-forming composition.

A bonding auxiliary is added mainly for the purpose of improving the adhesion between a substrate or a resist and the resist underlying film-forming composition to prevent the resist from peeling off particularly in the development. Specific examples of bonding auxiliaries include chlorosilanes, such as trimethylchlorosilane, dimethylmethylolchlorosilane, methyldiphenylchlorosilane, and chloromethyldimethylchlorosilane; alkoxysilanes, such as trimethylmethoxysilane, dimethyldiethoxysilane, methyldimethoxysilane, dimethylmethylolethoxysilane, diphenyldimethoxysilane, and phenyltriethoxysilane; silazanes, such as hexamethyldisilazane, N,N'-bis(trimethylsilyl) urea, dimethyltrimethylsilylamine, and trimethylsilylimidazole; silanes, such as methyloltrichlorosilane, γ-chloropropyltrimethoxysilane, γ-aminopropyltriethoxysilane, and γ-glycidoxypropyltrimethoxysilane; heterocyclic compounds, such as benzotriazole, benzimidazole, indazole, imidazole, 2-mercaptobenzimidazole, 2-mercaptobenzothiazole, 2-mercaptobenzoxazole, urazole, thiouracil, mercaptoimidazole, and mercaptopyrimidine; and urea or thiourea compounds, such as 1,1-dimethylurea and 1,3-dimethylurea. The bonding auxiliary is incorporated usually in an amount of less than 5% by mass, preferably less than 2% by mass, based on the total mass of the solid components in the resist underlying film-forming composition.

[Resist Underlying Film, Method for Producing a Patterned Substrate, and Method for Producing a Semiconductor Device]

Hereinbelow, a resist underlying film produced using the resist underlying film-forming composition of the present invention, a method for producing a patterned substrate, and a method for producing a semiconductor device will be described.

(Resist Underlying Film)

The resist underlying film of the present invention may be produced by applying the above-described resist underlying film-forming composition onto a semiconductor substrate and baking the applied composition.

Examples of semiconductor substrates to which the resist underlying film-forming composition of the present invention is applied include a silicon wafer, a germanium wafer, and compound semiconductor wafers, such as gallium arsenide, indium phosphide, gallium nitride, indium nitride, and aluminum nitride.

When a semiconductor substrate having an inorganic film formed on the surface thereof is used, the inorganic film is formed by, for example, an ALD (atomic layer deposition) method, a CVD (chemical vapor deposition) method, a reactive sputtering method, an ion plating method, a vacuum deposition method, or a spin coating method (spin on glass: SOG). Examples of the inorganic films include a polysilicon film, a silicon oxide film, a silicon nitride film, a BPSG (Boro-Phospho Silicate Glass) film, a titanium nitride film, a titanium nitride oxide film, a tungsten film, a gallium nitride film, and a gallium arsenide film.

The resist underlying film-forming composition of the present invention is applied onto the above-mentioned semiconductor substrate by an appropriate application method, such as a spinner or a coater. Then, the applied composition is baked using a heating means, such as a hotplate, to form a resist underlying film. Conditions for baking are appropriately selected from those at a baking temperature of 100 to 400° C. for a baking time of 0.3 to 60 minutes. Preferred conditions for baking are those at a baking temperature of 120 to 350° C. for a baking time of 0.5 to 30 minutes, and more preferred conditions are those at a baking temperature of 150 to 300° C. for a baking time of 0.8 to 10 minutes.

The thickness of the formed resist underlying film is within the range of, for example, 0.001 μm (1 nm) to 10 μm, preferably 0.002 μm (2 nm) to 1 μm, more preferably 0.005 μm (5 nm) to 0.5 μm (500 nm). When the temperature during the baking is lower than the above range, crosslinking is likely to unsatisfactorily proceed. On the other hand, when the temperature during the baking is higher than the above range, the resist underlying film is likely to suffer decomposition due to heat.

(Method for Producing a Patterned Substrate)

The method for producing a patterned substrate has the following steps. Usually, a patterned substrate is produced by forming a photoresist layer on a resist underlying film. With respect to the photoresist formed on the resist underlying film by application and baking according to a known method, there is no particular limitation as long as it is sensitive to a light used in the exposure. Any of a negative photoresist and a positive photoresist may be used. There are, for example, a positive photoresist comprising a novolak resin and 1,2-naphthoquinonediazidosulfonate; a chemical amplification photoresist comprising a binder having a group which is decomposed due to an acid to increase the alkali solubility, and a photo-acid generator; a chemical amplification photoresist comprising a low-molecular weight compound which is decomposed due to an acid to increase the alkali solubility of the photoresist, an alkali-soluble binder, and a photo-acid generator; and a chemical amplification photoresist comprising a binder having a group which is decomposed due to an acid to increase the alkali solubility, a low-molecular weight compound which is decomposed due to an acid to increase the alkali solubility of the photoresist, and a photo-acid generator. Examples thereof include trade name: V146G, manufactured by JSR Corporation; trade name: APEX-E, manufactured by Shipley Company, Inc.; trade name: PAR710, manufactured by Sumitomo Chemical Co., Ltd.; and trade names: AR2772, SEPR430, manufactured by Shin-Etsu Chemical Co., Ltd. Further, they include fluorine atom-containing polymer photoresists described in, for example, Proc. SPIE, Vol. 3999, 330-334 (2000), Proc. SPIE, Vol. 3999, 357-364 (2000), and Proc. SPIE, Vol. 3999, 365-374 (2000).

Exposure through a mask (reticle) for forming a predetermined pattern is conducted, and, for example, an i-line, a KrF excimer laser, an ArF excimer laser, an EUV (extreme ultraviolet light) or an EB (electron beam) is used. In development, an alkaline developer is used, and conditions are appropriately selected from those at a development temperature of 5 to 50° C. for a development time of 10 to 300 seconds. As an alkaline developer, there may be used, for example, an aqueous solution of an alkali, e.g., an inorganic alkali, such as sodium hydroxide, potassium hydroxide, sodium carbonate, sodium silicate, sodium metasilicate, or aqueous ammonia; a primary amine, such as ethylamine or n-propylamine; a secondary amine, such as diethylamine or di-n-butylamine; a tertiary amine, such as triethylamine or methyldiethylamine; an alcohol amine, such as dimethylethanolamine or triethanolamine; a quaternary ammonium salt, such as tetramethylammonium hydroxide, tetraethylammonium hydroxide, or choline; or a cyclic amine, such as pyrrole or piperidine. Further, there may be used the above-mentioned aqueous alkali solution which has added thereto an alcohol, such as isopropyl alcohol, or a surfactant, such as a nonionic surfactant, in an appropriate amount. Of these, a preferred developer is a quaternary ammonium salt, and further preferred are tetramethylammonium hydroxide and choline. Further, for example, a surfactant may be added to the above developer. Instead of the method using an alkaline developer, a method may be used in which development is conducted using an organic solvent, such as butyl acetate, to develop a portion of the photoresist in which the alkali dissolution rate is not improved. A substrate having the resist patterned may be produced through the above-mentioned steps.

Then, using the formed resist pattern as a mask, the resist underlying film is subjected to dry etching. In this instance, when the above-mentioned inorganic film is formed on the surface of the semiconductor substrate used, the surface of the inorganic film is exposed, and, when the inorganic film is not formed on the surface of the semiconductor substrate used, the surface of the semiconductor substrate is exposed. Then, the substrate is subjected to processing step by a known method (such as a dry etching method), producing a semiconductor device.

EXAMPLES

Next, the present invention will be described in more detail with reference to the following Examples, which should not be construed as limiting the scope of the present invention.

The apparatus and other conditions used in the measurement of the weight average molecular weight of the polymers obtained in the following Synthesis Examples are shown below.

Apparatus: HLC-8320GPC, manufactured by Tosoh Corp.
GPC Column: Shodex [registered trademark]-Asahipak [registered trademark] (Showa Denko K.K.)
Column temperature: 40° C.
Flow rate: 0.35 mL/minute
Eluent: Tetrahydrofuran (THF)
Standard sample: Polystyrene (Tosoh Corp.)

Synthesis Example 1

10.00 g of methyl isocyanurate (Me-ICA) synthesized in accordance with the method described in the specification of the patent publication (WO2017/208910), 14.49 g of potassium carbonate (manufactured by Kanto Chemical Co., Inc.), 20.48 g of allyl chloroacetate (manufactured by Sigma-Aldrich Co., LLC.), and 40.00 g of N,N-dimethylformamide (manufactured by Kanto Chemical Co., Inc.) were charged, and the resultant mixture was stirred at 60° C. for 25 hours. 100.00 g of toluene (manufactured by Kanto Chemical Co., Inc.) was charged thereto, and the resultant mixture was subjected to filtration. 100.00 g of water was added to the filtrate, followed by separation at 50° C. To the obtained organic layer was further added 100.00 g of water, followed by separation at 50° C. Concentration of the obtained organic layer gave 20.51 g of the intended product (methyldiallyl acetate isocyanurate: Me-DAAICA) represented by formula (M-1) in a yield of 86.5%. The $^1$H NMR (500 MHz, DMSO-$d_6$) measurement of the compound showed: 85.92 (m, 2H), 5.32 (dd, 2H), 5.23 (dd, 2H), 4.62 (d, 4H), 4.66 (s, 4H), 3.23 (s, 3H).

[Chemical formula 20]

Formula (M-1)

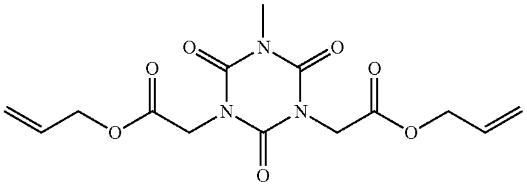

Synthesis Example 2

20.51 g of Me-DAAICA obtained in Synthesis Example 1 and 153.83 g of chloroform (manufactured by Kanto Chemical Co., Inc.) were charged, and to the resultant mixture was added 38.52 g of m-chloroperbenzoic acid (manufactured by Tokyo Chemical Industry Co., Ltd.). The reaction was conducted for 71 hours, and the reaction was ascertained to have reached a constant weight. After completion of the reaction, 205.10 g of chloroform (manufactured by Kanto Chemical Co., Inc.) and 410.20 g of 5% by weight sodium hydrogencarbonate (manufactured by Kanto Chemical Co., Inc.) were added to the reaction mixture. The resultant mixture was subjected to separation, and into the obtained organic layer was charged 205.10 g of 10% by weight sodium sulfite (manufactured by Kanto Chemical Co., Inc.). Thereafter, the resultant mixture was subjected to separation again, and into the obtained organic layer was charged 410.20 g of 5% by weight sodium hydrogencarbonate (manufactured by Kanto Chemical Co., Inc.). Then, the resultant mixture was subjected to separation, and the obtained organic layer was washed with 205.10 g of water twice. Concentration and drying of the organic layer followed by the column purification gave 10.46 g of the intended product (methyldiglycidyl acetate isocyanurate: Me-DAGICA) represented by formula (A-1) in a yield of 46.6%. The $^1$H NMR (500 MHZ, DMSO-$d_6$) measurement of the obtained compound showed: 84.63 (s, 4H), 4.49 (dd, 2H), 3.94 (dd, 2H), 3.23 (m, 2H), 3.23 (s, 3H), 2.79 (m, 2H), 2.65 (m, 2H).

[Chemical formula 21]

Formula (A-1)

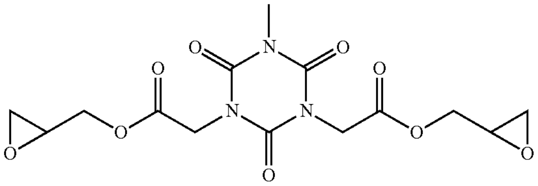

Example 1

To 4.00 g of Me-DAGIA obtained in Synthesis Example 2, 2.40 g of dithiodiglycolic acid, and 0.20 g of ethyltriphenylphosphonium bromide in a reaction flask was added 26.42 g of propylene glycol monomethyl ether, and the resultant mixture was heated at 100° C. in a nitrogen atmosphere while stirring for 24 hours, obtaining a reaction product which corresponds to formula (C-1). The reaction product had a weight average molecular weight Mw of 1,800, as determined by GPC using a conversion calibration curve obtained from the standard polystyrene. In formula (C-1), a:b=100:120 (molar ratio).

To 5.59 g of the solution of the reaction product which corresponds to formula (C-1) (having a content of solid components of 17.2% by weight) were added 0.04 g of pyridinium trifluoromethanesulfonate as a crosslinking acid catalyst, 0.001 g of a surfactant (product name: MEGAFACE [trade name] R-40, manufactured by DIC Corporation; fluorine surfactant), 12.47 g of propylene glycol monomethyl ether, and 1.90 g of propylene glycol monomethyl ether acetate to prepare a resist underlying film-forming composition for lithography in the form of a solution.

[Chemical formula 22]

Formula (C-1)

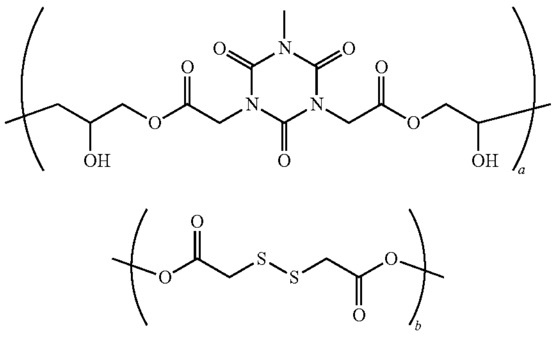

Synthesis Example 3

27.50 g of methoxymethyl isocyanurate (MOM-ICA) synthesized in accordance with the method described in the specification of the patent publication (WO2018/034323), 32.93 g of potassium carbonate (manufactured by Kanto Chemical Co., Inc.), 46.55 g of allyl chloroacetate (manufactured by Sigma-Aldrich Co., LLC.), and 110.00 g of N,N-dimethylformamide (manufactured by Kanto Chemical Co., Inc.) were charged, and the resultant mixture was stirred at 60° C. for 4 hours. Since the reaction reached a constant weight, 257.00 g of toluene (manufactured by Kanto Chemical Co., Inc.) was charged, and the resultant mixture was subjected to filtration. 257.00 g of water was added to the filtrate, followed by separation at 50° C. Concentration of the obtained organic layer gave 53.11 g of the intended product (methoxymethyldiallyl acetate isocyanurate: MOM-DAAICA) represented by formula (M-2) in a yield of 90.5%. The $^{1}$H NMR (500 MHZ, DMSO-$d_6$) measurement of the obtained compound showed: 85.91 (m, 2H), 5.33 (dd, 2H), 5.24 (dd, 2H), 5.20 (s, 2H), 4.65 (d, 4H), 4.64 (s, 4H), 3.30 (s, 3H).

[Chemical formula 23]

Formula (M-2)

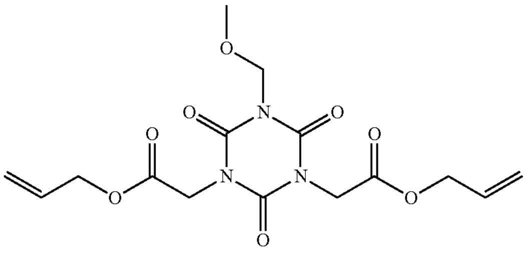

Synthesis Example 4

53.11 g of MOM-DAAICA obtained in Synthesis Example 3 and 398.33 g of chloroform (manufactured by Kanto Chemical Co., Inc.) were charged, and to the resultant mixture was added 91.63 g of m-chloroperbenzoic acid (manufactured by Tokyo Chemical Industry Co., Ltd.). The reaction was conducted for 76 hours, and the reaction was ascertained to have reached a constant weight. After completion of the reaction, 531.10 g of chloroform (manufactured by Kanto Chemical Co., Inc.) and 1,062.20 g of 5% by weight sodium hydrogencarbonate (manufactured by Kanto Chemical Co., Inc.) were added to the resultant reaction mixture. The resultant mixture was subjected to separation, and into the obtained organic layer was charged 531.10 g of 10% by weight sodium sulfite (manufactured by Kanto Chemical Co., Inc.). Thereafter, the resultant mixture was subjected to separation again, and into the obtained organic layer was charged 1,062.20 g of 5% by weight sodium hydrogencarbonate (manufactured by Kanto Chemical Co., Inc.). Then, the resultant mixture was subjected to separation, and the obtained organic layer was washed with 531.11 g of water twice. Concentration and drying of the organic layer followed by the column purification gave 41.66 g of the intended product (methoxymethyldiglycidyl acetate isocyanurate: MOM-DAGICA) represented by formula (A-7) in a yield of 72.2%. The H NMR (500 MHZ, DMSO-$d_6$) measurement of the obtained compound showed: 85.20 (s, 2H), 4.65 (s, 4H), 4.49 (dd, 2H), 3.95 (dd, 2H), 3.31 (s, 3H), 3.22 (m, 2H), 2.80 (m, 2H), 2.66 (m, 2H).

[Chemical formula 24]

Formula (A-7)

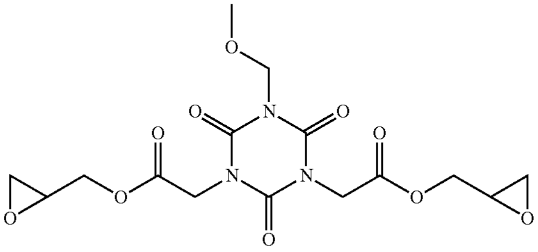

Example 2

To 5.50 g of MOM-DAGICA obtained in Synthesis Example 4, 2.90 g of dithiodiglycolic acid, and 0.25 g of ethyltriphenylphosphonium bromide in a reaction flask was added 8.69 g of propylene glycol monomethyl ether, and the resultant mixture was heated at 70° C. in a nitrogen atmosphere while stirring for 24 hours, obtaining a reaction product which corresponds to formula (C-2). The reaction product had a weight average molecular weight Mw of 2,300, as determined by GPC using a conversion calibration curve obtained from the standard polystyrene. In formula (C-2), a:b=100:120 (molar ratio).

To 5.13 g of the solution of the reaction product which corresponds to formula (C-2) (having a content of solid components of 18.7% by weight) were added 0.04 g of pyridinium trifluoromethanesulfonate as a crosslinking acid catalyst, 0.001 g of a surfactant (product name: MEGAFACE [trade name] R-40, manufactured by DIC Corporation; fluorine surfactant), 12.93 g of propylene glycol monomethyl ether, and 1.90 g of propylene glycol monomethyl ether acetate to prepare a resist underlying film-forming composition for lithography in the form of a solution.

[Chemical formula 25]

Formula (C-2)

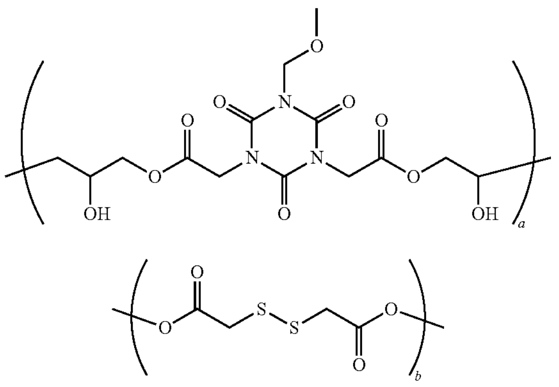

Synthesis Example 5

38.70 g of triscarboxymethyl isocyanurate (TAICA) synthesized in accordance with the method described in the specification of U.S. Pat. No. 3,230,220, 300.00 g of N-methyl-2-pyrrolidone (manufactured by Kanto Chemical Co., Inc.), 70.91 g of allyl bromide (manufactured by Tokyo Chemical Industry Co., Ltd.), and 79.38 g of potassium carbonate (manufactured by Kanto Chemical Co., Inc.) were charged, and the temperature of the resultant mixture was increased to 80 to 90° C. Then, a reaction was conducted for 2 hours, and the reaction was ascertained to have reached a constant weight. After completion of the reaction, 580.50 g of toluene (manufactured by Kanto Chemical Co., Inc.) was added to the reaction mixture. The resultant mixture was subjected to filtration, and the filtrate was washed with 580.50 g of water three times. The organic layer was concentrated and dried and then, 387.00 g of ethanol (manufactured by Kanto Chemical Co., Inc.) was charged into the concentrate, and the resultant mixture was stirred at 20 to 30° C. for 30 minutes. After the stirring was stopped, the mixture was subjected to filtration. Drying the obtained crystal gave 44.32 g of the intended product (triallyl acetate isocyanurate: TAAICA) represented by formula (M-3) in a yield of 85.2%.

[Chemical formula 26]

Formula (M-3)

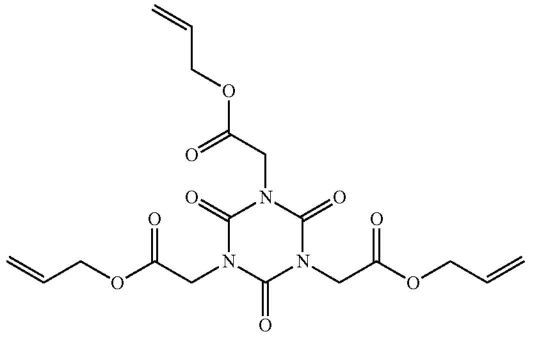

Synthesis Example 6

44.32 g of TAAICA synthesized in Synthesis Example 5 and 443.20 g of chloroform (manufactured by Kanto Chemical Co., Inc.) were charged, and to the resultant mixture was added 125.06 g of m-chloroperbenzoic acid (manufactured by Tokyo Chemical Industry Co., Ltd.). The reaction was conducted for 47 hours. After completion of the reaction, 88.64 g of chloroform (manufactured by Kanto Chemical Co., Inc.) was added to the reaction mixture. Further, the resultant mixture was washed with 886.40 g of 5% sodium hydrogencarbonate (manufactured by Kanto Chemical Co., Inc.). Subsequently, the mixture was washed with 443.20 g of 10% sodium sulfite (manufactured by Kanto Chemical Co., Inc.) and 886.40 g of 5% sodium hydrogencarbonate (manufactured by Kanto Chemical Co., Inc.), and further washed with 443.20 g of water twice. Concentration and drying of the mixture followed by the column purification gave 41.31 g of the intended product (triglycidyl acetate isocyanurate: TAGICA) represented by formula (M-2) in a yield of 83.7%.

[Chemical formula 27]

Formula (A-19)

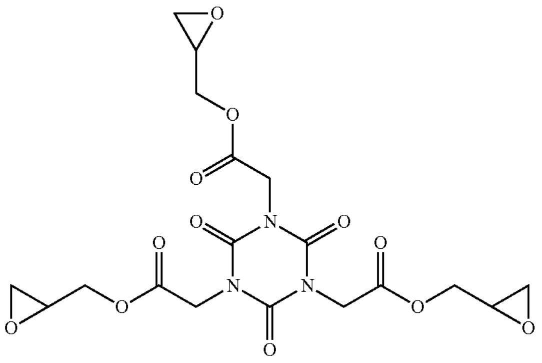

Example 3

To 9.00 g of TAGICA obtained in Synthesis Example 6, 6.99 g of dithiodiglycolic acid, and 0.53 g of ethyltriphenylphosphonium bromide in a reaction flask was added 66.11 g of propylene glycol monomethyl ether, and the resultant mixture was heated at 70° C. in a nitrogen atmosphere while stirring for 23 hours, obtaining a reaction product which corresponds to formula (C-3). The reaction product had a weight average molecular weight Mw of 3,000, as determined by GPC using a conversion calibration curve obtained from the standard polystyrene. In formula (C-3), a:b=100:200 (molar ratio).

To 8.31 g of the solution of the reaction product which corresponds to formula (C-3) (having a content of solid components of 11.56% by weight) were added 0.04 g of pyridinium trifluoromethanesulfonate as a crosslinking acid catalyst, 0.001 g of a surfactant (product name: MEGAFACE [trade name] R-40, manufactured by DIC Corporation; fluorine surfactant), 9.75 g of propylene glycol monomethyl ether, and 1.90 g of propylene glycol monomethyl ether acetate to prepare a resist underlying film-forming composition for lithography in the form of a solution.

[Chemical formula 28]

Formula (C-3)

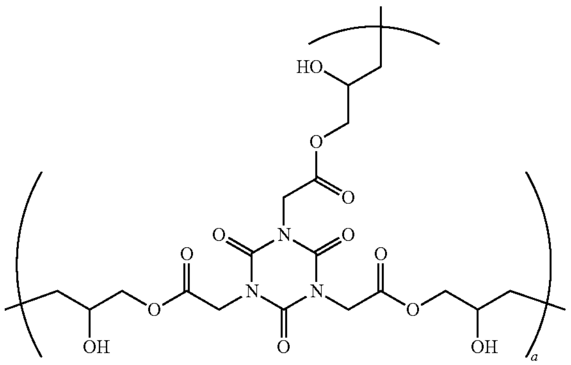

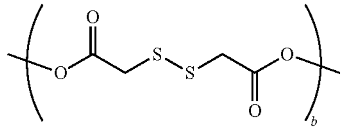

Comparative Example 1

To 12.00 g of monomethyldiglycidyl isocyanurate (product name: Me-DGIC, manufactured by Shikoku Chemicals Corporation; 50% by weight propylene glycol monomethyl ether solution), 5.26 g of dithiodiglycolic acid, and 0.45 g of ethyltriphenylphosphonium bromide in a reaction flask was added 1.80 g of propylene glycol monomethyl ether, and the resultant mixture was heated at 70° C. in a nitrogen atmosphere while stirring for 21 hours. The resultant reaction product solution was diluted with 39.01 g of propylene glycol monomethyl ether, obtaining a reaction product which corresponds to formula (D-1). The reaction product had a weight average molecular weight Mw of 1,700, as determined by GPC using a conversion calibration curve obtained from the standard polystyrene. In formula (D-1), a:b=100:120 (molar ratio).

To 5.41 g of the solution of the reaction product which corresponds to formula (D-1) (having a content of solid components of 17.8% by weight) were added 0.04 g of pyridinium trifluoromethanesulfonate as a crosslinking acid catalyst, 0.001 g of a surfactant (product name: MEGA-FACE [trade name] R-40, manufactured by DIC Corporation; fluorine surfactant), 12.65 g of propylene glycol monomethyl ether, and 1.90 g of propylene glycol monomethyl ether acetate to prepare a resist underlying film-forming composition for lithography in the form of a solution.

[Chemical formula 29]

Formula (D-1)

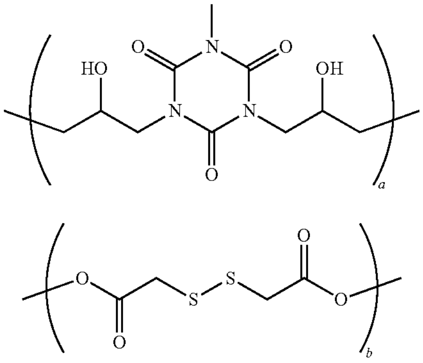

Comparative Example 2

To 4.00 g of 1,3,5-tris(2,3-epoxypropyl) isocyanurate (product name: TEPIC-SS, manufactured by Nissan Chemical Corporation), 6.09 g of dithiodiglycolic acid, and 0.37 g of ethyltriphenylphosphonium bromide in a reaction flask was added 10.46 g of propylene glycol monomethyl ether, and the resultant mixture was heated at 65° C. in a nitrogen atmosphere while stirring for 22 hours. The resultant reaction product solution was diluted with 31.39 g of propylene glycol monomethyl ether, obtaining a reaction product which corresponds to formula (D-2). The reaction product had a weight average molecular weight Mw of 2,800, as determined by GPC using a conversion calibration curve obtained from the standard polystyrene. In formula (D-2), a:b=100:250 (molar ratio).

To 7.40 g of the solution of the reaction product which corresponds to formula (D-2) (having a content of solid components of 13.0% by weight) were added 0.04 g of pyridinium trifluoromethanesulfonate as a crosslinking acid catalyst, 0.001 g of a surfactant (product name: MEGA-FACE [trade name] R-40, manufactured by DIC Corporation; fluorine surfactant), 10.66 g of propylene glycol monomethyl ether, and 1.90 g of propylene glycol monomethyl ether acetate to prepare a resist underlying film-forming composition for lithography in the form of a solution.

[Chemical formula 30]

Formula (D-2)

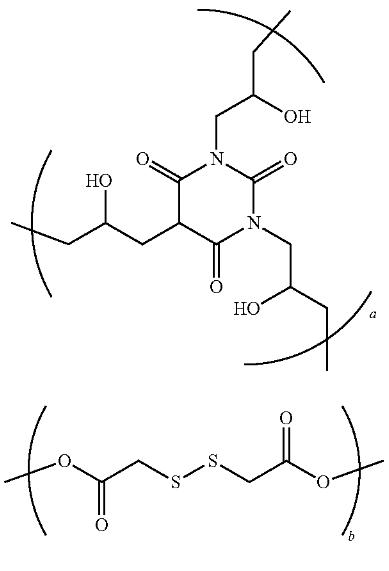

[Evaluation of Resist Solvent Resistance]

Each of the resist underlying film-forming compositions for lithography prepared in Examples 1 to 3 and Comparative Examples 1 and 2 was applied onto a silicon wafer using a coater/developer (CLEAN TRACK ACT-8, manufactured by Tokyo Electron Limited) (spin coating) so that the resultant film had a thickness of about 100 nm, and the film was baked in a baking unit at 215° C. or 250° C. for 60 seconds. Then, for evaluating the resist solvent resistance of the resist underlying film formed on the wafer, the formed resist underlying film was immersed in OK73 Thinner (manufactured by Tokyo Ohka Kogyo Co., Ltd.; propylene glycol monomethyl ether/propylene glycol monomethyl ether acetate=70/30 mixed solvent) using a coater/developer for one minute, subjected to spin drying and then baked at 100° C. for 30 seconds. The thickness of the resist underlying film was measured using an interference thickness meter (Lamda Ace VM-3210, manufactured by SCREEN Semiconductor Solutions Co., Ltd.) before and after the immersion in the mixed solvent.

The resist solvent resistance was evaluated by the thickness reduction ratio (%) of the resist underlying film removed by the immersion in the solvent, which was calculated by the equation: ((Thickness of the film before immersed in the solvent)−(Thickness of the film after immersed in the solvent))÷(Thickness of the film before immersed in the solvent)×100. A film having a thickness reduction ratio of about 1% or less is considered to have a satisfactory resist solvent resistance. The thickness reduction ratio (%) of the resist underlying films is shown in [Table 1].

TABLE 1

[Table 1]

| Examples | Baking temperature | Thickness reduction ratio |
|---|---|---|
| Example 1 | 250° C./60 sec. | 0.2% |
| Example 2 | 250° C./60 sec. | 0.1% |
| Example 3 | 250° C./60 sec. | 0.2% |
| Comparative Example 1 | 250° C./60 sec. | 0.1% |
| Comparative Example 2 | 215° C./60 sec. | 0.1% |

As apparent from the above results, the films obtained in Examples 1 to 3 exhibit satisfactory solvent resistance to the resist solvent, and therefore can be advantageously used as a resist underlying film.

[Evaluation of Optical Constant]

Each of the resist underlying film-forming compositions for lithography prepared in Examples 1 to 3 and Comparative Examples 1 and 2 was applied onto a silicon wafer using a spin coater so that the resultant film had a thickness of about 50 nm, and the film was baked on a hotplate at 215° C. or 250° C. for 60 seconds. The n value (refractive index) and k value (attenuation coefficient) of the obtained resist underlying film at a wavelength of 193 nm were determined using a spectroscopic ellipsometer (VUV-VASE, manufactured by J. A. Woolam Co., Inc.). The results are shown in Table 2.

[Evaluation of Etching Selective Ratio]

Each of the resist underlying film-forming compositions for lithography prepared in Examples 1 to 3 and Comparative Examples 1 and 2 was applied onto a silicon wafer so that the resultant film had a thickness of about 130 nm, and the film was baked on a hotplate at 215° C. or 250° C. for 60 seconds. The obtained resist underlying film was subjected to dry etching by nitrogen gas for 60 seconds using a dry etching machine (RIE-10NR, manufactured by Samco Inc.) to determine the dry etching rate of the resist underlying film.

An antireflection coating agent for semiconductor lithography (product name: DUV30J, manufactured by Nissan Chemical Corporation) was applied onto a silicon wafer so that the resultant film had a thickness of about 150 nm, and the film was baked on a hotplate at 215° C. for 60 seconds. The obtained film was subjected to dry etching by nitrogen gas for 60 seconds using a dry etching machine (RIE-10NR, manufactured by Samco Inc.) to determine the dry etching rate of the resist underlying film.

The dry etching rate ratio (etching selective ratio) of the resist underlying film obtained from each of the resist underlying film-forming compositions for lithography prepared in Examples 1 to 3 and Comparative Examples 1 and 2, which was calculated when the dry etching rate of the antireflection coating agent for semiconductor lithography (DUV30J) was taken as 1.00, is shown in [Table 2].

TABLE 2

[Table 2]

| Examples | Optical constant (n/k) | Etching selective ratio |
|---|---|---|
| Example 1 | 1.92/0.15 | 7.00 |
| Example 2 | 1.90/0.13 | 7.24 |
| Example 3 | 1.90/0.12 | 6.68 |
| Comparative Example 1 | 1.98/0.26 | 6.20 |
| Comparative Example 2 | 1.95/0.25 | 6.00 |

As apparent from the above results, the films in Examples 1 to 3 have appropriate n/k values at a wavelength of 193 nm, and therefore the compositions have a function as an antireflection coating agent, which provide a resist underlying film for lithography that suppresses the reflection from the substrate side. Further, the films in Examples 1 to 3 have an even higher etching selective ratio than that of the films in Comparative Examples 1 and 2. As the result, the resist underlying film-forming composition for lithography obtained by the present invention permits reduction of the etching time for dry etching of the resist underlying film, and therefore permits suppression of an unfavorable phenomenon of decrease of the thickness of the resist film at the time of removing the resist underlying film by dry etching. Further, the reduction of the dry etching time may lead to suppression of etching damage, which is unfavorable to the substrate for the resist underlying film, and therefore, the resist underlying film obtained from the composition of the present invention is especially useful for providing a resist underlying film.

INDUSTRIAL APPLICABILITY

The resist underlying film-forming composition of the present invention provides a resist underlying film having especially high dry etching rate.

The invention claimed is:

1. A resist underlying film-forming composition comprising a solvent, and an epoxy addition product, which is a reaction product of an epoxy addition product-forming compound and a compound represented by the following formula (1):

Formula (1)

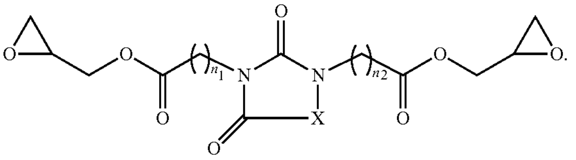

wherein, in formulae (1), X is a divalent organic group represented by formula (2), (3), or (4) below, and each of n1 and n2 independently represents an integer of 1 to 10:

Formula (2)

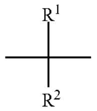

Formula (3)

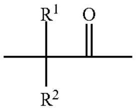

Formula (4)

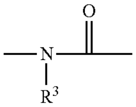

wherein, in formulae (2), (3), and (4), each of $R^1$ and $R^2$ independently represents a hydrogen atom, an alkyl group having 1 to 10 carbon atoms and being optionally interrupted by an oxygen atom or a sulfur atom, an alkenyl group having 2 to 10 carbon atoms and being optionally interrupted by an oxygen atom or a sulfur atom, an alkynyl group having 2 to 10 carbon atoms and being optionally interrupted by an oxygen atom or a sulfur atom, a benzyl group, or a phenyl group, wherein the phenyl group is optionally substituted with at least one monovalent functional group selected from the group consisting of an alkyl group having 1 to 6 carbon atoms, a halogen atom, an alkoxy group having 1 to 10 carbon atoms, a nitro group, a cyano group, and an alkylthio group having 1 to 6 carbon atoms, and $R^3$ represents a hydrogen atom, an alkyl group having 1 to 10 carbon atoms and being optionally interrupted by an oxygen atom or a sulfur atom, an alkenyl group having 3 to 10 carbon atoms and being optionally interrupted by an oxygen atom or a sulfur atom, an alkynyl group having 3 to 10 carbon atoms and being optionally interrupted by an oxygen atom or a sulfur atom, a benzyl group, or a phenyl group, wherein when $R^3$ is a phenyl group, the phenyl group is optionally substituted with at least one monovalent functional group selected from the group consisting of an alkyl group having 1 to 6 carbon atoms, a halogen atom, an alkoxy group having 1 to 10 carbon atoms, a nitro group, a cyano group, and an alkylthio group having 1 to 6 carbon atoms, wherein the epoxy addition product-forming compound is a carboxylic acid-containing compound or a thiol group-containing compound, and wherein the carboxylic acid-containing compound is a dicarboxylic acid having at least one sulfur atom.

2. The resist underlying film-forming composition according to claim 1, wherein the dicarboxylic acid having at least one sulfur atom is an aliphatic dicarboxylic acid.

3. The resist underlying film-forming composition according to claim 1, further comprising a crosslinking catalyst.

4. The resist underlying film-forming composition according to claim 1, further comprising a crosslinking agent.

5. The resist underlying film-forming composition according to claim 1, further comprising a surfactant.

6. A resist underlying film which is a baked product of an applied film comprising the resist underlying film-forming composition according to claim 1.

7. A method for producing a patterned substrate, comprising the steps of: applying the resist underlying film-forming composition according to claim 1 onto a semiconductor substrate and baking the applied composition to form a resist underlying film; applying a resist onto the resist underlying film and baking the applied resist to form a resist film; subjecting the semiconductor substrate covered with the resist underlying film and the resist to exposure; and subjecting the exposed resist film to development to perform patterning.

8. A method for producing a semiconductor device, comprising the steps of:

forming a resist underlying film comprising the resist underlying film-forming composition according to claim 1 on a semiconductor substrate;

forming a resist film on the resist underlying film;

irradiating the resist film with a light or an electron beam and subjecting the resultant resist film to development to form a resist pattern;

etching the resist underlying film through the formed resist pattern to form a patterned resist underlying film; and processing the semiconductor substrate using the patterned resist underlying film.

9. The resist underlying film-forming composition according to claim 1, wherein the epoxy addition product has a weight average molecular weight of 1,000 to 100,000.

10. The resist underlying film-forming composition according to claim 1, further comprising at least one selected from the group consisting of a light absorber, a rheology modifier, and a bonding auxiliary.

11. The method according to claim 8, wherein a thickness of the formed resist underlying film is within a range of 0.001 μm to 10 μm.

12. The resist underlying film-forming composition according to claim 1, wherein, in formula (1), X is represented by formula (4).

13. The resist underlying film-forming composition according to claim 1, wherein, in formula (1), n, and n2 are 1, and $R^3$ is an alkyl group having 1 to 5 carbon atoms and being optionally interrupted by an oxygen atom.

* * * * *